(12) United States Patent
Narusawa et al.

(10) Patent No.: US 10,206,622 B2
(45) Date of Patent: Feb. 19, 2019

(54) BIOLOGICAL INFORMATION ANALYZING SYSTEM, BIOLOGICAL INFORMATION PROCESSING SYSTEM, AND BIOLOGICAL INFORMATION ANALYZING DEVICE

(71) Applicant: Seiko Epson Corporation, Tokyo (JP)

(72) Inventors: Atsushi Narusawa, Chino (JP);
Shinichiro Watanabe, Koto-ku (JP)

(73) Assignee: Seiko Epson Corporation, Tokyo (JP)

( * ) Notice: Subject to any disclaimer, the term of this patent is extended or adjusted under 35 U.S.C. 154(b) by 595 days.

(21) Appl. No.: 14/833,331

(22) Filed: Aug. 24, 2015

(65) Prior Publication Data
US 2016/0058391 A1 Mar. 3, 2016

(30) Foreign Application Priority Data

Aug. 27, 2014 (JP) ................. 2014-172690

(51) Int. Cl.
| | | |
|---|---|---|
| *A61B 5/04* | (2006.01) | |
| *A61B 5/00* | (2006.01) | |
| *A61B 5/024* | (2006.01) | |
| *A61B 5/0404* | (2006.01) | |
| *A61B 5/046* | (2006.01) | |
| *A61B 5/11* | (2006.01) | |

(52) U.S. Cl.
CPC .......... *A61B 5/681* (2013.01); *A61B 5/02438* (2013.01); *A61B 5/0404* (2013.01); *A61B 5/721* (2013.01); *A61B 5/046* (2013.01); *A61B 5/11* (2013.01); *A61B 2562/0219* (2013.01)

(58) Field of Classification Search
USPC ........................................... 600/518; 607/116
See application file for complete search history.

(56) References Cited

U.S. PATENT DOCUMENTS

| | | | |
|---|---|---|---|
| 2004/0147969 A1* | 7/2004 | Mann .................... | A61B 5/0215 607/17 |
| 2011/0144510 A1* | 6/2011 | Ryu ....................... | A61B 5/042 600/509 |
| 2013/0060154 A1 | 3/2013 | Morita | |

FOREIGN PATENT DOCUMENTS

| | | |
|---|---|---|
| JP | 2002-291707 A | 10/2002 |
| JP | 2013-055982 A | 3/2013 |

* cited by examiner

*Primary Examiner* — Nicole F Johnson
(74) *Attorney, Agent, or Firm* — ALG Intellectual Property, LLC

(57) ABSTRACT

A biological information analyzing system includes: a reception unit receiving pulse wave information which is collected by a pulse wave measurement device worn by a user; a processing unit performing analysis processing with respect to atrial fibrillation of the user on the basis of the pulse wave information and generating browsing information of an analysis result of the analysis processing; and an output unit outputting the generated browsing information.

16 Claims, 16 Drawing Sheets

PULSE AC

BIOLOGICAL INFORMATION ANALYZING SYSTEM, BIOLOGICAL INFORMATION PROCESSING SYSTEM, AND BIOLOGICAL INFORMATION ANALYZING DEVICE

This application claims priority to Japanese Patent Application No. 2014-172690, filed Aug. 27, 2014, the entirety of which is hereby incorporated by reference.

BACKGROUND

1. Technical Field

The present invention relates to a biological information analyzing system, a biological information processing system, a biological information analyzing device, and the like.

2. Related Art

Atrial fibrillation which is a cardiovascular disease causes a risk of brain infarction in which blood may clot in the heart, and thus it is necessary to perform a medical treatment in an early stage. In the related art, in general, a Holter electrocardiographic monitor is worn by a patient for 24 hours to 48 hours (typically 24 hours), and thus the inspection of the atrial fibrillation confirms the onset of atrial fibrillation from an electrocardiogram during the time period.

However, in the initial atrial fibrillation, the onset frequency thereof decreases, and on occasion the Holter electrocardiographic inspection within 48 hours misses the diagnosis of atrial fibrillation. In addition, in asymptomatic atrial fibrillation, a patient does not feel symptomatic and rarely visits a medical center, and thus the asymptomatic atrial fibrillation becomes severe (for example, the brain infarction occurs) and is usually known as the atrial fibrillation. Furthermore, the reason that the Holter electrocardiographic monitor is not able to be used for a long period of time is because it is necessary to attach a plurality of electrodes to the chest, and skin is irritated by an electrode or a tape for fastening the electrode. In addition, recently, an electrocardiographic monitor in which a record is able to be kept for 40 days has been used, but the problem of the irritation has not been solved, and thus it is not practical to continuously use the electrocardiographic monitor for a long period of time.

On the other hand, in JP-A-2013-55982, a method is disclosed in which a parameter corresponding to an RR interval is accurately obtained from pulse wave information, and thus atrial fibrillation is diagnosed on the basis of the pulse wave information. The pulse wave information, for example, is able to be acquired by a pulse wave sensor such as a photoelectric sensor. Therefore, a device including the pulse wave sensor, for example, is able to be realized as a wristwatch type wearable device, and thus it is possible to continuously wear the device for a long period of time while suppressing the possibility of skin irritation or the like.

As in JP-A-2013-55982, it is possible to wear the device for a long period of time (for example, approximately 3 days to 10 days) by using the pulse wave information, and thus it is possible to suitably detect initial atrial fibrillation or the like.

However, in JP-A-2013-55982, a determination method of the atrial fibrillation based on the pulse wave information is disclosed, but a method for suitably presenting a determination result to a browsing user is not sufficiently described. For example, when the browsing user is a medical doctor, it is important to select or process suitable information in order for the doctor to easily make the determination. Specifically, from a viewpoint of easiness of making a blood clot, it is useful to calculate and present not only information of simply indicating whether or not the atrial fibrillation occurs but also information of a continuous onset time or a total onset time. Alternatively, it may be important to output the detection result of the atrial fibrillation in association with other information. The other information herein, for example, is information relevant to the movement of a user at the time of onset, or before and after the onset.

SUMMARY

An advantage of some aspects of the invention is to provide a biological information analyzing system which generates and outputs suitable browsing information on the basis of an analysis result of atrial fibrillation using pulse wave information, a biological information processing system, a biological information analyzing device, and the like.

An aspect of the present invention relates to a biological information analyzing system including: a reception unit receiving pulse wave information which is collected by a pulse wave measurement device worn by a user; a processing unit performing analysis processing with respect to atrial fibrillation of the user on the basis of the pulse wave information and generating browsing information of an analysis result of the analysis processing; and an output unit outputting the generated browsing information.

According to the aspect of the invention, the analysis processing is performed with respect to the atrial fibrillation on the basis of the pulse wave information, and the browsing information is generated from the result of the analysis processing and is output. The atrial fibrillation is determined from the pulse wave information, and thus it is possible to wear a device for a long period of time, compared to an electrocardiographic monitor such as a Holter electrocardiograph. Further, the browsing information is generated from the analysis result and is output, and thus it is possible to present the analysis result to the browsing user in various modes.

In the aspect of the invention, the processing unit may generate the browsing information including total onset time information of the atrial fibrillation.

With this configuration, it is possible to include information indicating a total onset time associated with the easiness of making a blood clot in the browsing information.

In the aspect of the invention, the processing unit may generate the browsing information including information which indicates a change in the total onset time information in chronological order.

With this configuration, it is possible to present a chronological change in a state relevant to the atrial fibrillation of the patient in an easy-to-understand mode.

In the aspect of the invention, the processing unit may generate the browsing information including continuous onset time information of the atrial fibrillation.

With this configuration, it is possible to include information indicating a continuous onset time associated with the easiness of making a blood clot in the browsing information.

In the aspect of the invention, the processing unit may generate the browsing information including information in which the continuous onset time information is associated with date and time.

With this configuration, it is possible to include information indicating not only a simple length of time but also an onset timing (a time period) of the atrial fibrillation in the browsing information.

In the aspect of the invention, the reception unit may receive body motion information of the user which is collected by the pulse wave measurement device or movement information of the user which is determined by the body motion information, and processing unit may generate the browsing information including information in which the body motion information or the movement information is associated with the analysis result of the atrial fibrillation.

With this configuration, it is possible to output suitable information in association with the analysis result of the atrial fibrillation.

In the aspect of the invention, the processing unit may generate the browsing information including information in which autonomic nerve activity information obtained on the basis of the pulse wave information is associated with the analysis result of the atrial fibrillation.

With this configuration, it is possible to output the suitable information in association with the analysis result of the atrial fibrillation.

In the aspect of the invention, the processing unit may generate the browsing information including information which indicates a degree of reliability of the analysis result of the atrial fibrillation.

With this configuration, it is possible to present a rough standard indicating a degree of reliability of the analysis result of the atrial fibrillation based on the pulse wave information to the browsing user.

In the aspect of the invention, the processing unit may generate the browsing information including information in which prescription medicine history information indicating medicine prescribed to the user is associated with the analysis result of the atrial fibrillation.

With this configuration, it is possible to output the suitable information in association with the analysis result of the atrial fibrillation.

In the aspect of the invention, the processing unit may generate the browsing information including information in which information indicating a change in pulse rate information of the user obtained on the basis of the pulse wave information in chronological order is associated with the analysis result of the atrial fibrillation.

With this configuration, it is possible to output the suitable information in association with the analysis result of the atrial fibrillation.

In the aspect of the invention, the processing unit may generate the browsing information including information in which event information indicating that the pulse wave measurement device has been operated is associated with the analysis result of the atrial fibrillation.

With this configuration, it is possible to output the suitable information in association with the analysis result of the atrial fibrillation.

In the aspect of the invention, the reception unit may receive setting information of a monitoring item relevant to the atrial fibrillation from a browsing user of the browsing information, the processing unit may extract information corresponding to the monitoring item as the browsing information from the analysis result, and the output unit outputs the extracted browsing information.

With this configuration, it is possible to suitably extract information estimating whether or not the browsing user requests the browsing on the basis of the setting information from the browsing user, and to present the information by including it in the browsing information.

In the aspect of the invention, the reception unit may receive the setting information indicating that the user is in a screening inspection step relevant to the atrial fibrillation from the browsing user, and the processing unit may extract at least one of continuous onset time information of the atrial fibrillation, information indicating whether or not the onset of the atrial fibrillation ends in a predetermined time period, and total onset time information of the atrial fibrillation as the monitoring item from the analysis result.

With this configuration, when it is notified that the user is in the screening inspection step from the browsing user, it is possible to extract the suitable information.

In the aspect of the invention, the reception unit may receive the setting information indicating that the user is in a medication effect confirmation step relevant to the atrial fibrillation from the browsing user, and the processing unit may extract at least one of onset history information of the atrial fibrillation, total onset time information of the atrial fibrillation, continuous onset time information of the atrial fibrillation, prescription medicine history information indicating medicine prescribed to the user, and information indicating a change in the pulse rate information of the user obtained on the basis of the pulse wave information in chronological order as the monitoring item from the analysis result.

With this configuration, when it is notified that the user is in the medication effect confirmation step from the browsing user, it is possible to extract the suitable information.

In the aspect of the invention, the reception unit may receive the setting information indicating that the user is in a catheter ablation effect confirmation step relevant to the atrial fibrillation from the browsing user, and the processing unit may extract at least one of onset history information of the atrial fibrillation, total onset time information of the atrial fibrillation, and continuous onset time information of the atrial fibrillation as the monitoring item from the analysis result.

With this configuration, when it is notified that the user is in the catheter ablation effect confirmation step from the browsing user, it is possible to extract the suitable information.

Another aspect of the invention relates to a biological information processing system including: a pulse wave measurement device which is worn by a user and collects pulse wave information; and an information processing device, wherein the information processing device, includes a reception unit receiving the pulse wave information collected by the pulse wave measurement device, a processing unit performing analysis processing with respect to atrial fibrillation of the user on the basis of the pulse wave information and generating browsing information of an analysis result of the analysis processing, and an output unit outputting the generated browsing information.

According to the aspect of the invention, the biological information processing system includes the pulse wave measurement device and the information processing device, the information processing device performs the analysis processing with respect to the atrial fibrillation by using the pulse wave information collected by the pulse wave measurement device, and generates the browsing information from the result of the analysis processing and outputs the information. The atrial fibrillation is determined from the pulse wave information, and thus it is possible to wear the pulse wave measurement device for a long period of time, compared to an electrocardiographic monitor such as a Holter electrocardiograph. Further, the browsing information is generated from the analysis result and is output, and thus it is possible to present the analysis result to the browsing user in various modes.

In the aspect of the invention, the biological information processing system may include a second information processing device operated by a browsing user, wherein the second information processing device may perform a browsing request of the analysis result with respect to the information processing device, the output unit of the information processing device may output the browsing information to the second information processing device according to the browsing request, and the second information processing device may display the browsing information output from the information processing device.

With this configuration, it is possible to include the second information processing device which is a device on the browsing user side in the biological information processing system, and the information processing device is able to suitably extract the information estimating whether or not the browsing user requests the browsing on the basis of the browsing request from the browsing user, and to present the information by including it in the browsing information.

Still another aspect of the invention relates to a biological information analyzing device including a pulse wave sensor acquiring pulse wave information of a user; a processing unit performing analysis processing with respect to atrial fibrillation of the user on the basis of the pulse wave information and generating browsing information of an analysis result of the analysis processing; and an output unit outputting the generated browsing information.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
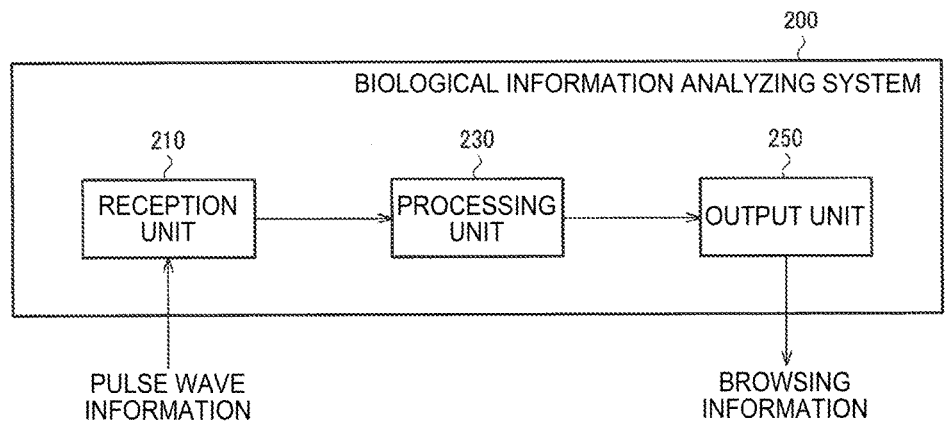
FIG. 1 is a configuration example of a biological information analyzing system according to this embodiment.

Hereinafter, this embodiment will be described. Furthermore, the content of the invention described in the appended claims is not limited to this embodiment described below. In addition, the entire configurations described in this embodiment are not limited as essential components of the invention.

1. Method of this Embodiment

First, a method of this embodiment will be described. As described above, as a disease relevant to the heart, atrial fibrillation has been known. The atrial fibrillation is an atrium spasm (a partial excitation contraction), and a cardiac chamber contracts at irregular intervals. For this reason, a blood flow stagnates, and thus a blood clot easily occurs by continuing the atrial fibrillation for a long period of time. As a result thereof, a serious symptomatic state leading to brain infarction or cardiac infarction occurs.

It is known that an RR interval (a heart rate interval) at the time of measuring an electrocardiogram becomes irregular at the onset of the atrial fibrillation. For this reason, in the related art, a Holter electrocardiograph is worn by a user for a time period such as 24 hours (or 48 hours), and the atrial fibrillation is detected from an electrocardiogram acquired at the time of wearing the Holter electrocardiograph. Furthermore, in the detection of the atrial fibrillation using the electrocardiogram, determination using appearance or disappearance of other waveforms such as a P wave or an f wave in addition to the RR interval is also performed, but the specific description thereof will be omitted herein.

However, the atrial fibrillation has a low onset frequency in an initial stage, and for example, a symptomatic state of the atrial fibrillation occurs once in three days, only for several hours. In this case, an onset time period and a wearing time period of the Holter electrocardiograph are not likely to overlap with each other, and thus the atrial fibrillation is not able to be detected. When the Holter electrocardiograph is able to be worn for a long period of time (for example, approximately 3 days to 10 days), it is possible to suitably detect the atrial fibrillation, but in the electrocardiographic measurement, it is necessary to attach an electrode to the skin of the user by using a tape or the like. For this reason, skin irritation easily occurs, and thus it is not easy to wear a device for measuring electrocardiogram for a long period of time.

In addition, in the atrial fibrillation, asymptomatic atrial fibrillation may be recognized in which a patient is not aware of a symptomatic state. In this case, it is difficult to conceive that the patient willingly has an inspection relevant to the atrial fibrillation, and according to a case, the symptomatic state progresses without any awareness of the atrial fibrillation, and thus a serious symptomatic state such as brain infarction may occur. On the other hand, it is preferable to periodically have a screening inspection for detecting the atrial fibrillation, but the Holter electrocardiograph has a problem of irritation as described above, and thus a frequent and periodic screening inspection is a great burden for the patient and is not easy.

On the other hand, in JP-A-2013-55982, a method of detecting the atrial fibrillation by using pulse wave information is disclosed. The pulse wave information is able to be acquired by a pulse wave sensor, and the pulse wave sensor, for example, is able to be realized by a photoelectric sensor. A specific mode of a pulse wave measurement device is different according to whether a light receiving unit receives transmitted light or reflected light, and the pulse wave measurement device may be fixed to a given portion of the user by a support member such as a band. Herein, the given portion may be a wrist, as will be described later with reference to FIG. 5A or the like, or may be other portions such as a finger, a neck, and an ankle.

For this reason, the pulse wave measurement device rarely has a problem of skin irritation, and is able to be continuously worn for a long period of time, compared to the electrocardiograph measurement device (an electrocardiographic monitor) such as the Holter electrocardiograph. When the pulse wave information is continuously acquired for a time period of approximately 3 days to 10 days, it is possible to detect the atrial fibrillation even in a state of a low onset frequency. In addition, the user who is not aware of the atrial fibrillation casually has a screening inspection.

The method of detecting the atrial fibrillation from the pulse wave information will be described later, and the method directly acquires whether or not the atrial fibrillation is detected at each processing timing (more specifically, whether the result is Yes or No in Step S410 of FIG. 17 described later). However, in order to multidirectionally verify an onset situation or onset causation, it is desired that a browsing user who browses the analysis result of the atrial fibrillation is presented not only such simple information but also more various information.

For example, when the browsing user is a medical doctor, the medical doctor makes a diagnosis of the state of the patient. For this reason, it is desired that the medical doctor who is the browsing user is provided with information in a mode in which the degree of seriousness of the patient is easily understood, or a mode of contributing to the determination of a medical treatment policy such as the determination of medicine to be dosed. Otherwise, it is necessary that the medical doctor analyzes data only from the detection or non-detection of the atrial fibrillation, and thus a burden for the medical doctor increases. For example, a blood clot occurs due to the stagnation of the blood, and thus a duration period of the stagnation, that is, a continuous onset time of the atrial fibrillation is also relevant to the easiness of making a blood clot or the size of the blood clot, and is information indicating the degree of seriousness of the symptomatic state. In this case, by further using the determination result obtained by the method described below, the continuous onset time information may be obtained, and the continuous onset time information may be included in browsing information.

In addition, it is considered that not only is the display mode of the analysis result of the atrial fibrillation determined but also the analysis result is presented in association with the other information. For example, information relevant to autonomic nerve activity may be obtained from the pulse wave information, or body motion information (or movement information of the user) may be obtained by using a body motion sensor, and it is possible to display the information in association with the analysis result of the atrial fibrillation.

That is, in analysis processing of the atrial fibrillation using the pulse wave information, it is important to determine in which mode the analysis result has to be browsed to the user, but such a point is not particularly considered in the method of the related art such as JP-A-2013-55982. Here, the applicant proposes a system which is able to present suitable information to the user.

Specifically, a biological information analyzing system 200 according to this embodiment, as illustrated in FIG. 1 includes a reception unit 210 which receives the pulse wave information collected by a pulse wave measurement device (corresponding to a pulse wave measurement device 100 of FIG. 2, and in a restricted sense, a wearable pulse wave measurement device) worn by the user, a processing unit 230 which performs analysis processing with respect to the atrial fibrillation of the user on the basis of the pulse wave information and generates browsing information of the analysis result of the analysis processing, and an output unit 250 which outputs the generated browsing information.

That is, in the processing unit 230 of the biological information analyzing system 200, on the basis of the pulse wave information received by the reception unit 210, the analysis processing described later is performed with respect to the atrial fibrillation, and the browsing information including the suitable information is generated from the analysis result. According to this, it is possible to output suitable browsing information, and thus it is possible to increase the convenience of the browsing user who uses (browses) the output result. Here, the "suitable information" may be information which is able to be versatilely used by considering the atrial fibrillation as the continuous onset time information described above, and the content of the information may be changed according to the state of the patient or the like. For example, the information included in the browsing information is able to be changed according to a patient in a medical treatment who has onset history of the atrial fibrillation and a patient who has a screening inspection without having any onset history.

Hereinafter, a configuration example of a system such as the biological information analyzing system will be described, and then a specific example of the information included in the browsing information will be described. After that, a method of determining (analyzing) the atrial fibrillation on the basis of the pulse wave information will be described in detail.

2. Configuration Example of System

As illustrated in FIG. 1, the biological information analyzing system 200 according to this embodiment includes the reception unit 210, the processing unit 230, and the output unit 250. The reception unit 210 acquires sensor information from the pulse wave sensor included in the pulse wave measurement device. Here, the pulse wave sensor is a sensor for detecting a pulse wave signal, and for example, a photoelectric sensor including a light emitting unit and a light receiving unit, and the like are considered. It is known that the pulse wave sensor such as a photoelectric sensor or other sensors (for example, an ultrasonic sensor) is able to be realized by various sensors, and these sensors are able to be widely applied to the pulse wave sensor of this embodiment.

The processing unit 230 performs the analysis processing with respect to the atrial fibrillation on the basis of the pulse wave information acquired by the reception unit 210, and generates the browsing information on the basis of the analysis result. The function of the processing unit 230 is able to be realized by various processors (a CPU or the like), hardware such as an ASIC (a gate array or the like), a program, and the like.

The output unit 250 outputs the browsing information generated by the processing unit 230. Various output modes of the output unit 250 are considered, and for example, the output unit 250 may transmit the browsing information to the other device through a network. In this case, the output unit 250 is realized by a communication unit. Here, the network is able to be realized by a Wide Area Network (WAN), a Local Area Network (LAN), and the like, and the network may be wired or wireless. Alternatively, the output unit 250 may print the browsing information, and in this case, the browsing user browses the printed browsing information in a paper medium or the like.

Figure 2:
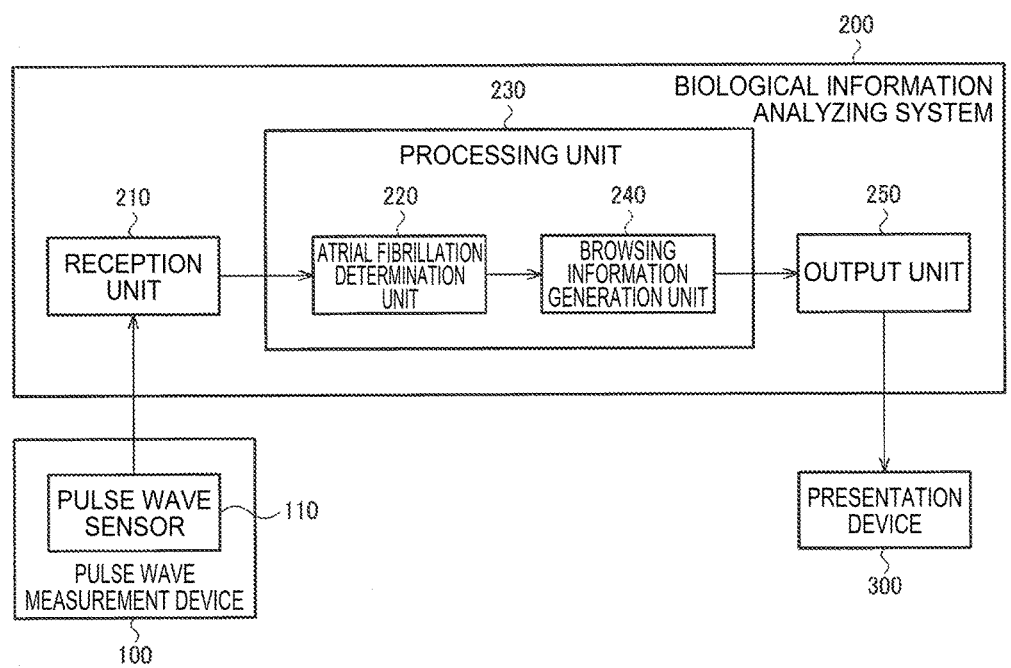
FIG. 2 is a specific configuration example of the biological information analyzing system according to this embodiment.

A specific configuration example of the system including the biological information analyzing system 200 is illustrated in FIG. 2. However, the biological information analyzing system 200 is not limited to the configuration of FIG. 2, and various modifications are able to be performed by omitting a part of constituents or adding other constituents. In an example of FIG. 2, the reception unit 210 of the biological information analyzing system 200 acquires the pulse wave information from the pulse wave measurement device 100 including a pulse wave sensor 110.

The processing unit 230 includes an atrial fibrillation determination unit 220 performing the analysis processing with respect to the atrial fibrillation, and a browsing information generation unit 240 generating the browsing information. The detail of the browsing information generated by the browsing information generation unit 240, and the detail of the configuration of the atrial fibrillation determination unit 220 and the processing in each unit will be respectively described later.

In addition, in the example of FIG. 2, the output unit 250 outputs the browsing information to another presentation device 300. That is, FIG. 2 is an example of transmitting the browsing information through a network as described above. In the presentation device 300, the browsing information acquired from the output unit 250 is presented with respect to the browsing user. In a restricted sense, the presentation device 300 includes a display unit, and may display the browsing information to the display unit.

Figure 3A:
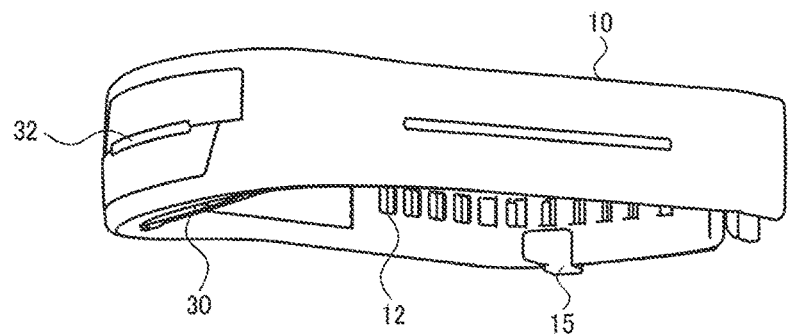
FIGS. 3A and 3B are configuration examples of a pulse wave measurement device.
Figure 3B:
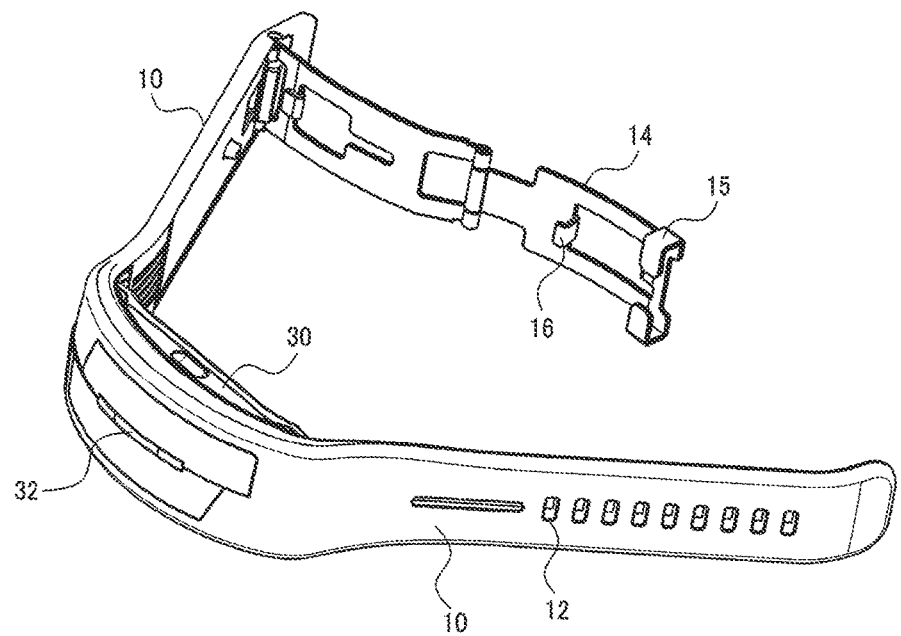
Figure 4:
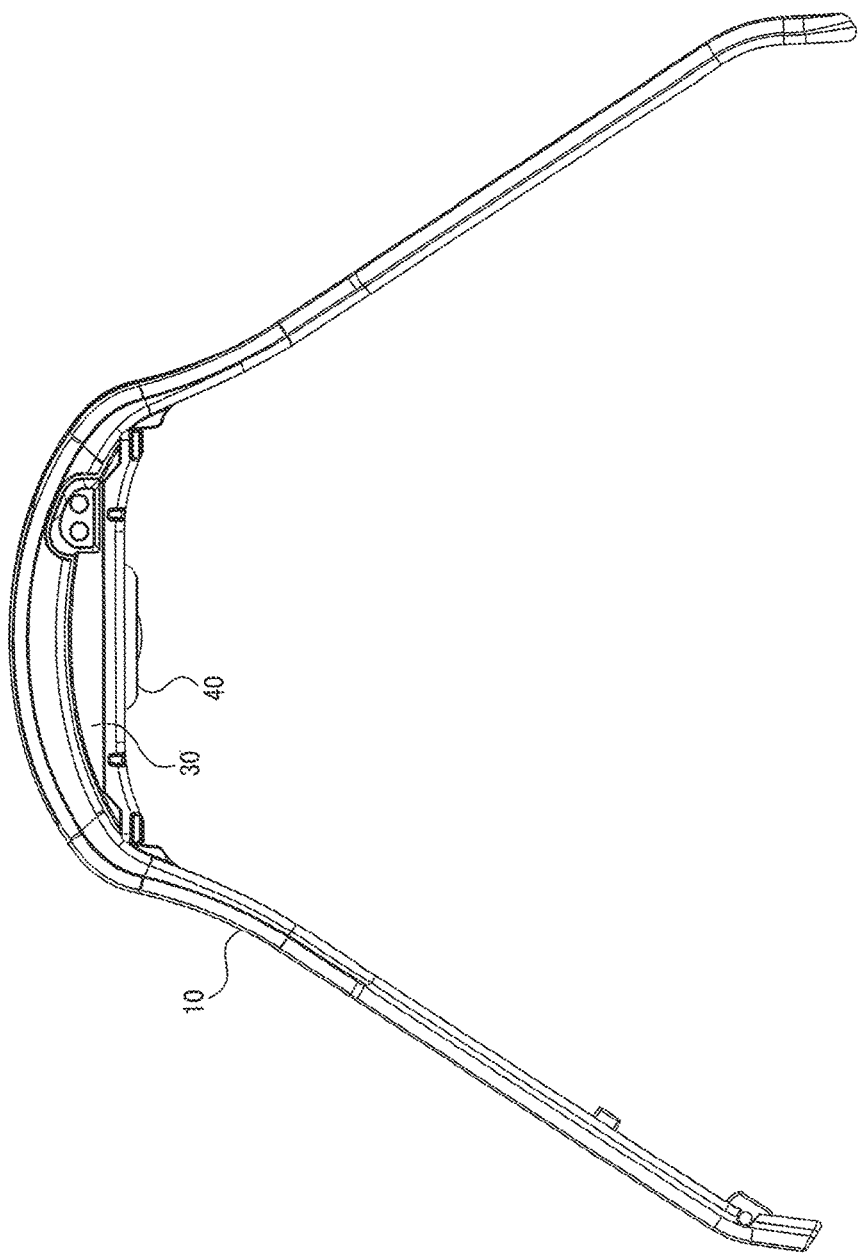
FIG. 4 is a configuration example of a pulse wave measurement device.

An example of an external view of the pulse wave measurement device 100 (a wearable device) collecting the pulse wave information is illustrated in FIGS. 3A to 4. The wearable device of this embodiment includes a band portion 10, a case portion 30, and a sensor unit 40. The case portion 30 is attached to the band portion 10. The sensor unit 40 is disposed on the case portion 30.

The band portion 10 is a portion for wearing the wearable device by being wound around the wrist of the user. The band portion 10 includes a band hole 12, and a buckle portion 14. The buckle portion 14 includes a band inserting portion 15 and a protrusion portion 16. The user inserts one end side of the band portion 10 to the band inserting portion 15 of the buckle portion 14, and inserts the protrusion portion 16 of the buckle portion 14 to the band hole 12 of the band portion 10, and thus wears the wearable device on the wrist.

The case portion 30 corresponds to a main body portion of the wearable device. In the case portion 30, various components of the wearable device such as a sensor unit 40 or a circuit board (not illustrated) are disposed. That is, the case portion 30 is a housing for containing these components.

A light emitting window portion 32 is disposed on the case portion 30. The light emitting window portion 32 is formed of a light receiving member. Then, a light emitting unit as an interface mounted on a flexible substrate is disposed in the case portion 30, and light from the light emitting unit is emitted to the outside of the case portion 30 through the light emitting window portion 32.

Figure 5C:
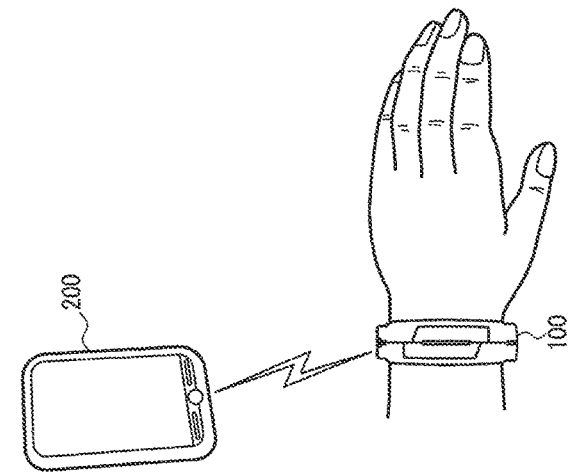
FIGS. 5A to 5C are specific implementations of the pulse wave measurement device and the biological information analyzing system.
Figure 5B:
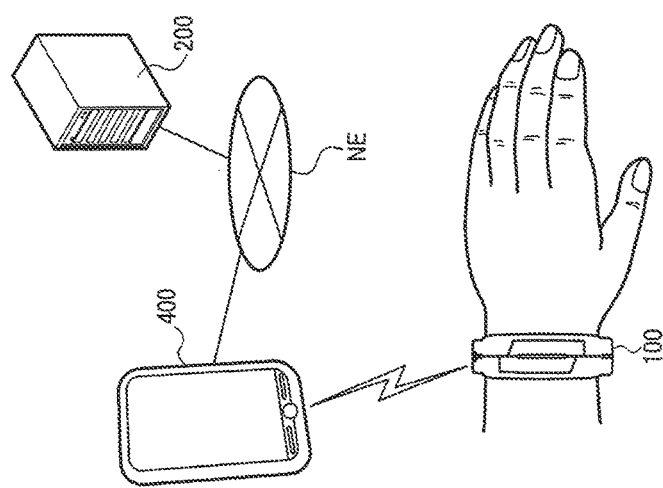
Figure 5A:
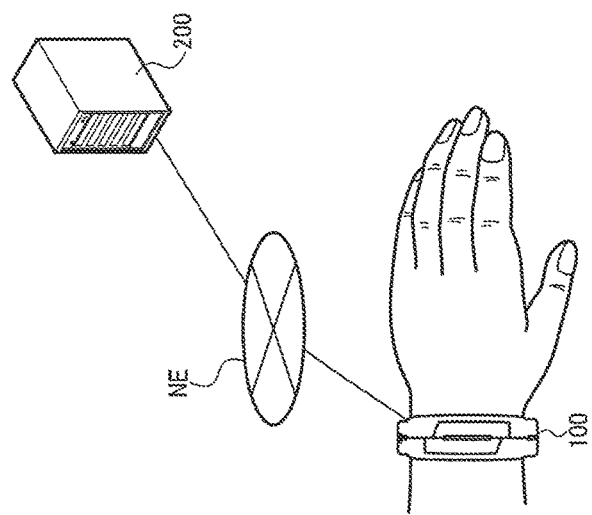

The wearable device is worn on the wrist of the user as illustrated in FIG. 5A or the like, and measurement of pulse wave information (in a broad sense, biological information) is performed in a state of being worn.

Next, an example of a specific device for realizing the biological information analyzing system 200 according to this embodiment will be described. The biological information analyzing system 200 according to this embodiment, for example, may be a server system. An example of this case is FIG. 5A, and the biological information analyzing system 200 which is the server system is connected to the pulse wave measurement device 100 through a network NE, and acquires the pulse wave information from the pulse wave measurement device 100. The wearable device (the pulse wave measurement device 100) worn by the user is required to be small and light, and thus there is a constraint on the processing performance of a battery or the processing unit in the device, or on the storage capacity of data. On the other hand, the server system has a comparatively small constraint on a resource, and thus it is possible to perform the analysis processing of the atrial fibrillation or the generation processing of the browsing information at a high rate or to retain more data (the pulse wave information, or the analysis result of the atrial fibrillation).

Furthermore, it is sufficient that the biological information analyzing system 200 is able to acquire the pulse wave information collected by the pulse wave measurement device 100, and thus the biological information analyzing system 200 is not limited to a configuration where the biological information analyzing system 200 is directly connected to the pulse wave measurement device 100. For example, as illustrated in FIG. 5B, the pulse wave measurement device 100 may be connected to a processing device 400, and the biological information analyzing system 200 may be connected to the processing device 400 through the network NE. As the processing device 400 of this case, for example, a mobile terminal device such as a smart phone which is used by the user provided with the pulse wave measurement device 100 is considered. Then, as the connection between the pulse wave measurement device 100 and the processing device 400, the same connection as that of the network NE may be used, or short-range wireless communication or the like is also able to be used.

In addition, the biological information analyzing system 200 according to this embodiment may be realized by not the server system but a processing device (in a restricted sense, a mobile terminal device) such as a smart phone. A configuration example of this case is FIG. 5C. The mobile terminal device such as the smart phone has a large constraint on the processing performance, a storage region, and battery capacity compared to the server system, but in consideration of recent improvement in the performance, it is considered that it is possible to ensure sufficient processing performance or the like. Accordingly, when a request for the processing performance or the like is satisfied, the smart phone or the like is able to be used as the biological information analyzing system 200 according to this embodiment as illustrated in FIG. 5C.

In addition, in consideration of improvement in terminal performance, an application mode, or the like, an embodiment in which the pulse wave measurement device 100 includes the biological information analyzing system 200 according to this embodiment is not be denied. In this case, the reception unit 210 receives (acquires) the information from the pulse wave sensor 110 in the same device. When the biological information analyzing system 200 is mounted on the pulse wave measurement device 100, in the biological information analyzing system 200, a request for data analysis, conservation, or the like which is targeted at a lot of users may decrease, and the biological information analyzing system 200 may be targeted at one or a few users using the pulse wave measurement device 100. That is, a possibility of satisfying the request of the user is sufficiently considered in the processing performance of the pulse wave measurement device 100 or the like.

That is, the method of this embodiment is able to be applied to the biological information analyzing device (a biological information measurement device, and a biological information detection device) including the pulse wave sensor 110 which acquires the pulse wave information of the user, the processing unit 230 which performs the analysis processing with respect to the atrial fibrillation of the user on the basis of the pulse wave information, and generates the browsing information of the analysis result of the analysis processing, and the output unit 250 which outputs the generated browsing information.

In addition, in the above description, the biological information analyzing system 200 is realized by any one of the server system, the processing device 400, and the pulse wave measurement device 100, but the configuration is not limited thereto. For example, the acquisition of the pulse wave information, the analysis processing of the atrial fibrillation, the generation processing of the browsing information, and the output processing may be realized by dispersion processing of a plurality of devices. Specifically, the biological information analyzing system 200 may be realized by at least two of the server system, the processing device 400, and the pulse wave measurement device 100. Alternatively, as in the presentation device 300 of FIG. 2, the other device may perform a part of the processing of the biological information analyzing system 200, and the biological information analyzing system 200 according to this embodiment is able to be realized by various devices (or a combination of the devices).

In the above description, the biological information analyzing system 200 is mainly described, but the configuration of this embodiment is able to be applied to the biological information processing system. Specifically, the configuration of this embodiment, as illustrated in FIG. 6, includes the pulse wave measurement device 100 worn by the user and collecting the pulse wave information, and an information processing device 500, and the information processing device 500 includes a reception unit 510 which receives the pulse wave information collected by the pulse wave measurement device 100, a processing unit 530 which performs the analysis processing with respect to the atrial fibrillation of the user on the basis of the pulse wave information, and generates the browsing information of the analysis result of the analysis processing, and an output unit 550 which outputs the generated browsing information.

Here, the information processing device 500, for example, is the server system of FIG. 5A or the like, and is a device for realizing the biological information analyzing system 200 described above. The reception unit 510, the processing unit 530, and the output unit 550 correspond to the reception unit 210, the processing unit 230, and the output unit 250, respectively. According to this, a system for collectively performing from the collection of the pulse wave information to the analysis of the atrial fibrillation based on the collected pulse wave information and the output of the browsing information based on the analysis result is able to be realized.

Figure 6:
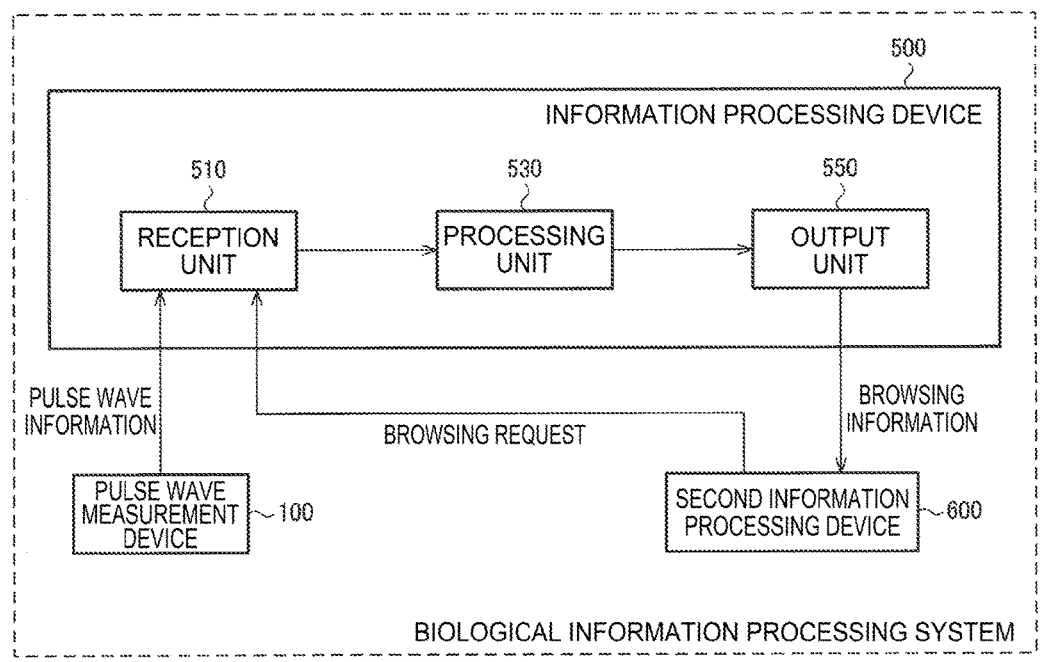
FIG. 6 is a configuration example of the biological information processing system according to this embodiment.

In addition, the biological information processing system, as illustrated in FIG. 6, may include a second information processing device 600 operated by the browsing user. Here, the second information processing device 600 corresponds to the presentation device 300 of FIG. 2, and for example, is a PC or the like operated by the medical doctor. Then, the second information processing device 600 performs a browsing request of the analysis result with respect to the information processing device 500, the output unit 550 of the information processing device 500 outputs the browsing information to the second information processing device 600 according to the browsing request, and the second information processing device 600 displays the browsing information output from the information processing device 500.

According to this, a system for collectively performing not only the analysis of the atrial fibrillation based on the collection of the pulse wave information and the collected pulse wave information and the output of the browsing information based on the analysis result, but also the display (presentation) of the output browsing information is able to be realized. At this time, when the browsing information is output and displayed with respect to the browsing request, it is possible to output the browsing information of the content according to the request at a timing according to the request of the browsing user who operates the second information processing device 600.

3. Specific Example of Browsing Information

The information included in the browsing information will be described in detail. First, as the information obtained from the analysis result by using a screen example of FIG. 7A, FIG. 7B, and the like, information which is a candidate for items (monitoring items) included in the browsing information will be described. After that, a method will be described in which when setting information is received from the browsing user, the monitoring items according to the setting information are extracted, and the browsing information is generated.

3.1 Detail of Each Monitoring Item

Figure 7A:
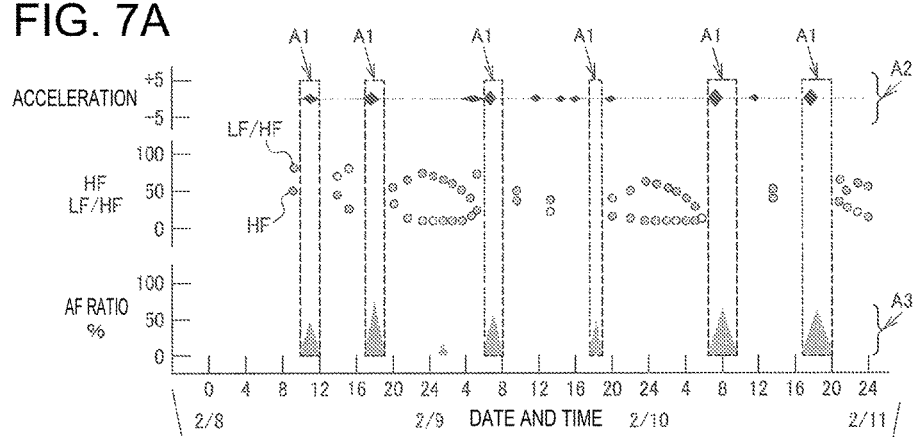
FIGS. 7A and 7B are screen examples at the time of presenting browsing information.
Figure 7B:
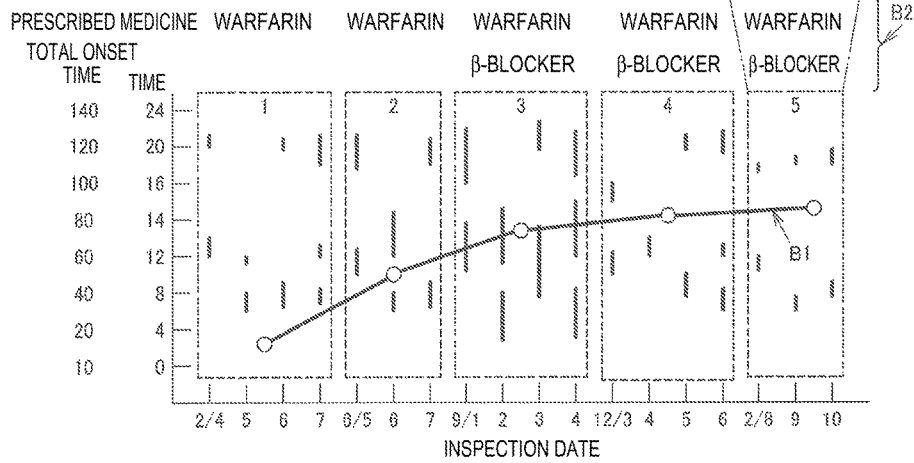

FIGS. 7A and 7B are display screen examples at the time of displaying the browsing information, FIG. 7A corresponds to the browsing information generated from a single inspection result, and FIG. 7B corresponds to the browsing information generated from a plurality of inspection results. That is, the processing unit 230 may generate first browsing information corresponding to the analysis result of the pulse wave information which is acquired in a first time period and second browsing information corresponding to the analysis result of the pulse wave information which is acquired in a time period longer than the first time period, and the output unit 250 may output the first browsing information and the second browsing information in combination.

Here, in a restricted sense, the first time period indicates a time period in which a single inspection is performed, and the second time period indicates a time period in which a plurality of inspections is performed. In addition, the "single inspection" indicates a unit in which the pulse wave information is continuously acquired by the pulse wave measurement device 100, and for example, the first time period corresponding to the single inspection is approximately a few days to 10 days. However, due to a constraint on the battery of the pulse wave measurement device 100 or the like, the first time period may be a blank time period in which the pulse wave information is not acquired in the single inspection. The blank time period is approximately a few minutes to a few hours and is sufficiently shorter than the first time period, and a span of a few days to a few months is not assumed. In contrast, when the plurality of inspections is performed, there is a blank time period of approximately a few days (in consideration of the efficiency of the inspection, a burden on the patient, or the like, for a few weeks) to a few months between the respective inspections.

According to this, when the first browsing information is displayed, as illustrated in FIG. 7A, it is possible to present specific information. In contrast, when the second browsing information is displayed, it is not easy to display the specific information, but it is easy to grasp the outline of the state of the patient such as a chronological change in the inspection result. In other words, the second browsing information is information indicating onset history information of the atrial fibrillation. That is, it is possible to present suitable browsing information according to the accuracy of the desired information of the browsing user. Furthermore, FIG. 7B is a screen collectively displaying five inspection results, and FIG. 7A is a screen displaying the detail of the five inspection results.

In a device on the browsing user side (the second information processing device 600 or the like), the first browsing information and the second browsing information may be concurrently displayed, but there is a constraint on the size of the display unit or the like. At this time, the browsing information to be displayed may be changed according to the operation of the browsing user. For example, a given operation is performed during the display of the screen of FIG. 7A corresponding to the first browsing information, and thus the display is transitioned to the display of the screen of FIG. 7B corresponding to the second browsing information. In addition, when any one of the plurality of inspections is selected during the display of the screen of FIG. 7B, the display may be transitioned to the display of the first browsing information indicating the detail of the corresponding inspection. FIG. 7A is information indicating the detail of the five inspections of FIG. 7B, and when the i-th (i=1 to 5) inspection is selected in FIG. 7B, the first browsing information corresponding to the i-th inspection is displayed. Here, it is considered that there are various operations for selecting the i-th inspection, and for example, in the screens of FIG. 7B, an operation such as clicking (or touching in case of a touch panel display) the rectangular frames indicating the i-th inspection may be used. It is assumed that the display control is performed in the second information processing device 600 (the presentation device 300), and may be performed by the biological information analyzing system 200 (the information processing device 500).

In addition, the processing unit 230 may generate the browsing information including the continuous onset time information of the atrial fibrillation. As described above, a time in which the atrial fibrillation continuously occurs is relevant to the easiness of making a blood clot, and the degree of seriousness of the symptomatic state which occurs due to the blood clot. For this reason, the continuous onset time information indicating the time in which the atrial fibrillation continuously occurs is obtained by the analysis processing, and the information is included in the browsing information, and thus it is possible to suitably present important information to the browsing user.

Here, the continuous onset time information may be information indicating a continuous onset time, and specifically, is information such as x minutes or y times. It is known that when the continuous onset time is approximately a few minutes to 1 hour, the blood clot rarely occurs, and when the continuous onset time is continued for approximately 5 hours, the blood clot easily occurs. Accordingly, in the continuous onset time acquired from one or a plurality of inspections results, information indicating the maximum time may be the continuous onset time information. The continuous onset time information of this case may be text information such as "Continuous Onset Time: 3 Hours", or may be shown by various graphs.

In addition, the processing unit 230 may generate the browsing information including information in which the continuous onset time information is associated with the date and time. Specifically, the information may be information such as "2 hours from 10:00 on February 8" or information such as "10:00 to 12:00 on February 8".

According to this, it is possible to present not only a simple length of the continuous onset time but also the time at which the atrial fibrillation occurs to the browsing user. The atrial fibrillation is classified as sympathetic nerve dependent type atrial fibrillation and vagus nerve dependent type atrial fibrillation, the former tends to easily occur in the day time, and the latter tends to easily occur in the night time. That is, by associating the continuous onset time information with the date and time, it is possible to know a temporal trend in which the atrial fibrillation occurs in a target patient in addition to a viewpoint of the easiness of making a blood clot described above. In particular, an effective medical agent is different between the sympathetic nerve dependent type atrial fibrillation and the vagus nerve dependent type atrial fibrillation, and thus the suitable classification is useful for determining a medical treatment policy.

In an example of FIG. 7A, a rectangular frame indicated by A1 (in particular, a horizontal width) corresponds to the continuous onset time information. A horizontal axis of FIG. 7A is a time, and according to such display, it is possible to present from what time of what day of the month and for how many hours the atrial fibrillation occurs in an easy-to-understand mode to the user. Naturally, the browsing information may be information in which data of combining the start date and time with the continuous onset time such as "2 hours from 10:00 on February 8" is listed by the number of onsets. In this case, which display screen is generated from the browsing information is arbitrary.

In addition, in an example of FIG. 7B, a horizontal axis is an inspection date, and a vertical axis is the time of one day. In this case, the one day (24 hours) corresponds to one line in an up and down direction, and the entire display screen is able to shown the onset situation of the atrial fibrillation in the entire inspection time period by only the lines corresponding to the number of days of the inspection date. In the example of FIG. 7B, the line is not drawn in a time period in which the atrial fibrillation does not occur, and the line is drawn in a time period in which the atrial fibrillation occurs. For example, in ⅔ of the first inspection, the atrial fibrillation occurs in a time period for a little more than 2 hours from 12:00 and in a time period for a little less than 2 hours from 20:00, and the atrial fibrillation does not occur in the other time period.

According to this, the continuous onset time is able to be indicated by the length of the continuous vertical line, and the onset date and time is able to be indicated by the position at which the vertical line is drawn. Specifically, the onset date is indicated by the position in a horizontal axis direction of the drawing position, and the onset time of the onset date is indicated by the position in the vertical axis direction. When the onset of the atrial fibrillation is over the day, the vertical line may not be continuous, but it is possible to display the continuous onset time information to be easily understood. For example, in the third inspection result, it is easily recognized that the vertical line tends to be long or the vertical line in an inspection time period is dense, and it is easily understood that the patient is not in a preferred state.

In addition, in consideration of presenting the onset history information of the atrial fibrillation, it is easy to compare results for each inspection. For example, in FIG. 7B, the line of the third inspection is long and the density of the ling is high, and thus the patient is not in a preferred state, but in the fourth inspection and the fifth inspection, the density of the line is low and the line is short. That is, by performing the display of FIG. 7B, it is possible to easily understand that the patient is getting better.

In the above description, the continuous onset time information is described, and the processing unit 230 may generate the browsing information including the total onset time information of the atrial fibrillation. As described above, when the atrial fibrillation continuously occurs, the blood clot easily occurs, and when the atrial fibrillation recedes, the occurrence of the blood clot is suppressed. In this sense, information directly relevant to the blood clot is the continuous onset time information.

However, as illustrated in FIGS. 7A and 7B, the atrial fibrillation may occur a plurality of times in a single inspection, and when the entire atrial fibrillation is displayed, the amount of information becomes excessive to the browing user. Accordingly, as information indicating a rough state of the patient, information indicating the total onset time obtained by accumulating the onset time of the atrial fibrillation may be used. As described above, the information does not include the information indicating whether the onset time is continuous or not, but the information is sufficient as information indicating the easiness of making a blood clot, and is able to decrease the amount of information, and thus the browsing user is able to extremely easily understand the information. Here, the total onset time information, for example, may be information in which one value is obtained for each inspection or information such as "Total Onset Time before Second Inspection: 8 Hours". In addition, when the inspection is performed a plurality of times, the accumulation processing of the onset time may be performed for each inspection, or may be performed by including the inspection of the past after the second inspection. That is, the total onset time information may be the same analysis result, may be information such as "Total Onset Time of First Inspection: 5 Hours" and "Total Onset Time of Second Inspection: 4 Hours", or may be information such as "Total Onset Time before First Inspection: 5 Hours" and "Total Onset Time before Second Inspection: 9 Hours". The former is preferable from a viewpoint of observing a change in each inspection, and the latter is preferable when it is considered that the length of the total onset time indicates the easiness of making a blood clot.

In addition, the processing unit 230 may generate the browsing information including information which indicates a change in the total onset time information in chronological order. According to this, it is possible to extremely clearly present the onset history information of the atrial fibrillation. A line graph illustrated by B1 in FIG. 7B is the change in the total onset time information in chronological order, and here, the total onset time information is subjected to the accumulation processing by including the inspection of the past, and each point of B1 indicates the total onset time. According to this, a change in a disease condition is easily understood by the slope of the broken line. According to the example of FIG. 7B, it is found that the patient is not in a preferred state from the first inspection to the third inspection in which a relatively large slope is continued, but the disease condition recovers in the fourth inspection and the fifth inspection in which the slope is extremely small.

In the above description, an example is described in which a directly analysis result of the analysis processing of the atrial fibrillation based on the pulse wave information described later, and information obtained therefrom are included in the browsing information. However, the browsing information is not limited thereto, and may include information in which information relevant to the analysis result is associated with the other information.

For example, the reception unit 210 receives body motion information of the user which is collected by the pulse wave measurement device 100 or movement information of the user which is determined by the body motion information, and the processing unit 230 may generate the browsing information in which the body motion information or the movement information is associated with the analysis result of the atrial fibrillation.

In this case, the pulse wave measurement device 100 includes the body motion sensor acquiring the body motion information. The body motion sensor is able to be realized by various sensors such as an acceleration sensor, a gyro sensor, and an orientation sensor. Here, the body motion information is information acquired by the body motion sensor, and information indicating the degree of the body movement of the user. As an example, the information may be information indicating the size of the acceleration.

In addition, the movement information is information obtained by the body motion information, and is information of the specific movement of the user. Various specific examples of the movement information are also considered, and for example, the information may be information indicating whether the user is in an awake state or in a sleep state, and in this case, the awake state may be segmented into a movement state and a rest state. In addition, the movement state is able to be segmented into a walking state, a running state, and the like, or the rest state is able to be segmented into a sitting state, a lying state, an erected state, and the like. Various methods of obtaining the movement information from the body motion information are known, and in this embodiment, these methods are able to be widely applied, and thus the specific description thereof is omitted.

The association of the body motion information (the movement information) with the analysis result, for example, may be performed on the basis of a timing at which each of the information items is acquired. For example, processing for matching the analysis result at a given time with the body motion information (the movement information) acquired at the given time (or a time sufficiently close thereto) is performed. Thus, a display example of the associated browsing information is A2 in FIG. 7A. In A1, the presence or absence of the onset of the atrial fibrillation as described above is indicated by the presence or absence of the rectangular frame, and according to this, an acceleration value (that is, the body motion information) at the corresponding timing is displayed as illustrated in A2. According to this, for the patient as a target it is easy to perform the association of the onset timing with the movement state of the user such as whether the atrial fibrillation easily occurs at the time of moving or the atrial fibrillation easily occurs at the time of resting or sleeping.

Figure 8A:
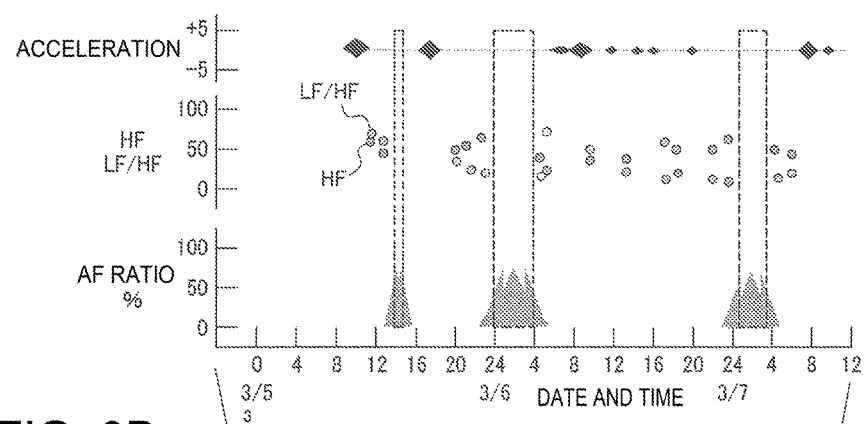
FIGS. 8A and 8B are screen examples at the time of presenting the browsing information.
Figure 8B:
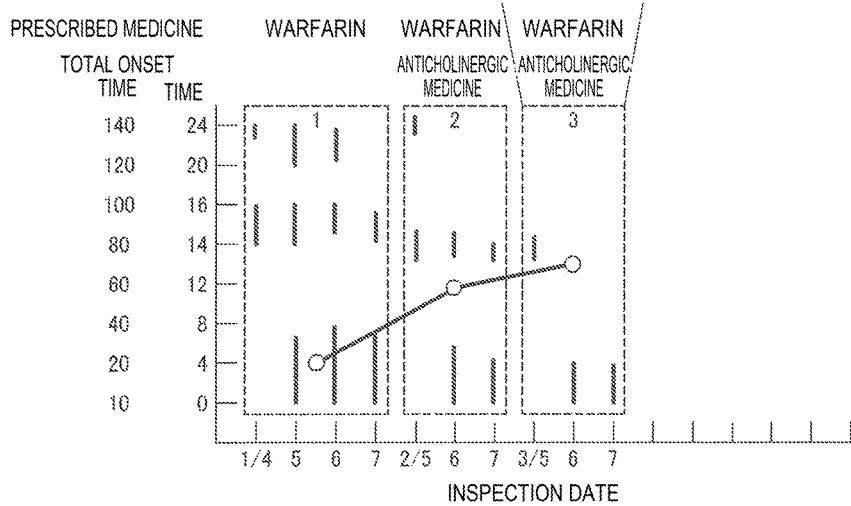

In the example of FIG. 7A, it is able to be determined that the atrial fibrillation occurs when the acceleration value increases, and thus the atrial fibrillation of the patient is able to be estimated as the sympathetic nerve dependent type atrial fibrillation. On the other hand, FIGS. 8A and 8B are examples of different patients, and in this case, it is able to be determined that the atrial fibrillation occurs when the acceleration value decreases. That is, the atrial fibrillation of the patient is able to be estimated as the vagus nerve dependent type atrial fibrillation.

In addition, in consideration that a vagus nerve as an automatic nerve system has a strong function as a parasympathetic nerve, it is useful to acquire information relevant to an active state of the automatic nerve of the user from a viewpoint of being easily classified as sympathetic nerve dependent type atrial fibrillation and vagus nerve dependent type atrial fibrillation. Accordingly, the processing unit 230 may generate the browsing information including information in which the autonomic nerve activity information obtained on the basis of the pulse wave information is associated with the analysis result of the atrial fibrillation.

Figure 9A:
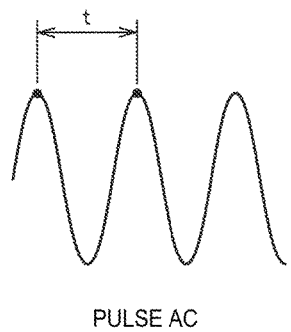
FIG. 9A is a diagram illustrating a pulse AC signal and a pulse interval.

In order to determine the autonomic nerve activity state from the pulse wave information, first, a pulse interval illustrated by t in FIG. 9A is measured for a certain time period, and thus chronological data of the pulse interval is acquired. The pulse interval is not constant but varies (fluctuates). Then, it is known that the variation occurs due to the activity of the sympathetic nerve and the activity of the parasympathetic nerve, and it is known that a variation degree due to the activity of the sympathetic nerve is different from a variation degree due to the activity of the parasympathetic nerve.

Figure 9B:
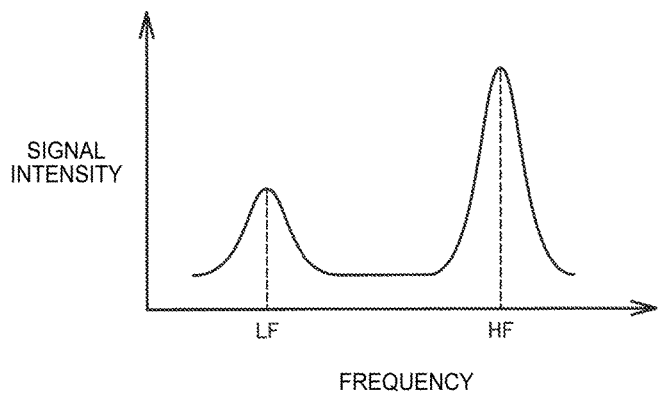
FIG. 9B is a diagram illustrating processing of obtaining LF and HF from pulse wave information.

Therefore, the chronological data of the pulse interval is subjected to frequency conversion. An example of the data after the frequency conversion is illustrated in FIG. 9B. As illustrated in FIG. 9B, a peak LF of a comparatively low frequency and a peak HF of a comparatively high frequency are acquired from the data after the frequency conversion.

LF indicates a slow change in the pulse interval, and mainly reflects the activity of the sympathetic nerve. On the other hand, HF indicates a fast change in the pulse interval which is faster than LF, and mainly reflects the activity of the parasympathetic nerve. Furthermore, in a narrow sense, LF reflects both of the sympathetic nerve and the parasympathetic nerve, and hereinafter, the reflection of the activity of the sympathetic nerve will be mainly described in order to simplify the description.

In consideration of such properties, a ratio of LF and HF (for example, a ratio of signal intensity at each peak) is obtained, and thus it is possible to determine whether the sympathetic nerve is dominant or the parasympathetic nerve is dominant in a measurement time period of the pulse wave information.

In the example of FIG. 7A or FIG. 8A, the value of HF and the value of LF/HF are obtained, and each of the values is associated with the analysis result relevant to the presence or absence of the onset of the atrial fibrillation in chronological order. Specifically, in a table, the values of HF and LF/HF are plotted by using a horizontal axis (a time) in common. In FIG. 7A, a vertical axis indicates the respective values of HF and LF/HF. It is able to be determined that when the value of HF increases, the parasympathetic nerve is dominant, and when the value of LF/HF increases, the sympathetic nerve is dominant.

Furthermore, when the atrial fibrillation occurs, a heart rate interval (the pulse interval) is in a random state. That is, in the onset of the atrial fibrillation, suitable information of the pulse interval is not obtained, and thus the value of the LF or HF is not also obtained. As a result thereof, as illustrated in FIG. 7A or FIG. 8A, within the frame of A1 in which the atrial fibrillation occurs, the values of LF and HF are not plotted.

In this case, the state of the autonomic nerve activity is not directly obtained at a timing at which the atrial fibrillation occurs, and thus presumption is performed from the information before and after the onset. For example, the values of HF and LF/HF before and after the onset may be complemented and processing for obtaining each value in the onset may be performed. In the example of FIG. 7A, it is possible to determine that the value of LF/HF increases, that is, the sympathetic nerve is dominant from the information before and after the onset, and thus the atrial fibrillation is able to be estimated as the sympathetic nerve dependent type atrial fibrillation, and in contrast, in the example of FIG. 8B, the value of HF increases, and thus the atrial fibrillation is able to be estimated as the vagus nerve dependent type atrial fibrillation.

In addition, the processing unit 230 may generate the browsing information including information in which prescription medicine history information indicating medicine prescribed to the user is associated with the analysis result of the atrial fibrillation. In the example of FIG. 7B, the type (or the name) of the prescribed medicine for each of the first inspection to the fifth inspection is displayed on an upper portion (B2) of the frame indicating the inspection. In the example of FIG. 7B, warfarin is prescribed after the first inspection and the second inspection, and β-blocker is prescribed in addition to the warfarin after the third inspection to the fifth inspection.

According to this, it is possible to confirm the history of the prescribed medicine from an inspection result screen, and it is possible to easily determine whether or not an effect is obtained by the prescribed medicine (whether or not the disease condition recovers, and thus the onset time of the atrial fibrillation or the like is shortened). For example, in the example of FIG. 7B, an improvement is not observed from the first inspection to the third inspection, and thus it is possible to determine that the effect is not sufficient by only prescribing the warfarin. In addition, after the third inspection, the β-blocker is prescribed, and the improvement is observed in the fourth inspection and the fifth inspection, and thus it is possible to determine that the β-blocker is effective.

Furthermore, in FIG. 8B, anticholinergic medicine is prescribed in addition to the warfarin after the second inspection. It is considered that this is because determination that the β-blocker is effective against sympathetic nerve dependent type atrial fibrillation with respect to the patient in FIGS. 7A and 7B, and a medical agent having an anticholinergic function is effective against vagus nerve dependent type atrial fibrillation with respect to the patient in FIGS. 8A and 8B is performed by the medical doctor. As described above, the body motion information or the autonomic nerve activity information is displayed in association with the analysis result of the atrial fibrillation, and thus it is possible to easily perform such determination by the medical doctor.

In addition, as described above, some patients with atrial fibrillation may have no noticeable symptoms. In the asymptomatic atrial fibrillation, the disease condition may be deteriorated while the patient is not aware of the atrial fibrillation, and thus not only the simple presence or absence of the onset but also information of whether or not the patient is aware of the onset is important. Therefore, the processing unit 230 may generate the browsing information including information in which event information indicating that the pulse wave measurement device 100 has been operated is associated with the analysis result of the atrial fibrillation.

Various operations of the pulse wave measurement device 100 are considered, and in a device illustrated in FIGS. 3A to 4, a button may be disposed on a side surface of a main body or the like, and the device may be operated by pressing the button. Alternatively, the pulse wave measurement device 100 includes a microphone or the like, and operation may be performed by a sound input (utterance) by the user insofar as the sound is able to be recognized. In addition, when the pulse wave measurement device 100 includes the body motion sensor such as an acceleration sensor, the device itself is able to recognize a tapping (hitting) operation, and the operation of this case is a tap operation. That is, here, the operation is able to be realized by an interface of various modes.

Figure 10:
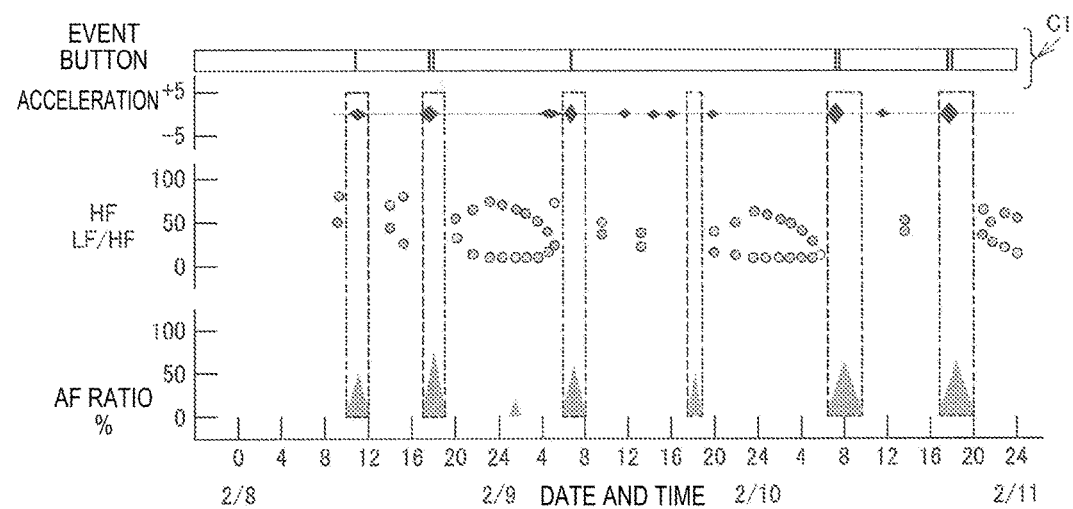
FIG. 10 is a screen example at the time of presenting the browsing information.

A display example of the browsing information of this case is FIG. 10, and an item of an "event button" is disposed in a position indicated by C1. In the position, a horizontal axis is commonly used in time, and a vertical line is displayed in a position of a timing at which the operation is performed by the user (the event button is pressed). In an example of FIG. 10, among six onsets of the atrial fibrillation in the inspection, a noticeable symptomatic state does not exist in one onset at approximately 18 o'clock on February 9, and the noticeable symptomatic state exists in the other five onsets.

In addition, the processing unit 230 may generate the browsing information including information in which information indicating that a change in the pulse rate information of the user in chronological order which is obtained on the basis of the pulse wave information is associated with the analysis result of the atrial fibrillation.

Figure 11A:
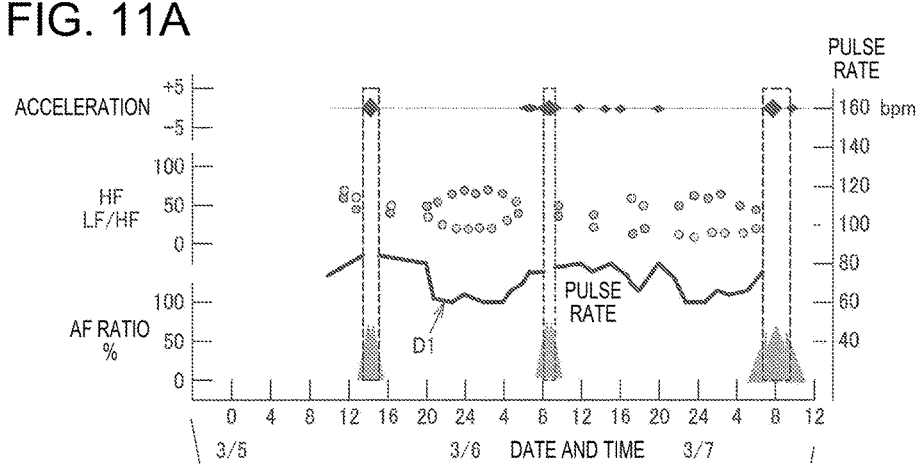
FIGS. 11A and 11B are screen examples at the time of presenting the browsing information.
Figure 11B:
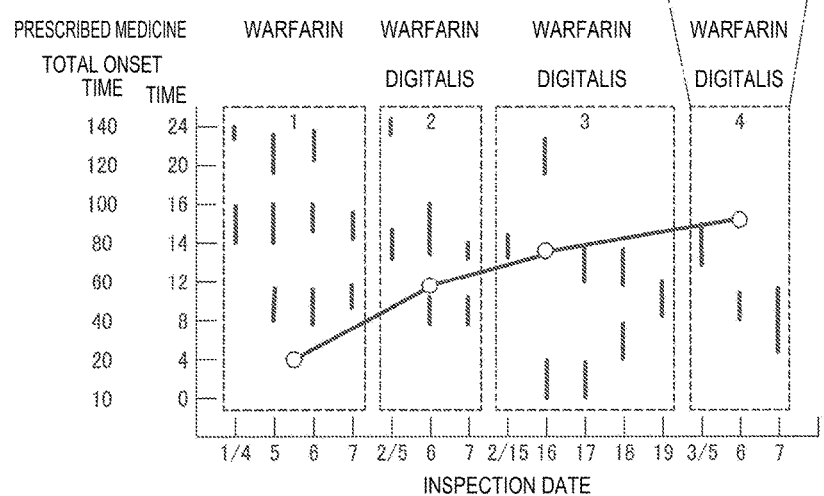

Here, the pulse rate information may be information relevant to the pulse rate, and specifically, may be the value of the pulse rate. A display example of the browsing information of this case is FIG. 11A. In the atrial fibrillation, in particular, in persistent atrial fibrillation described later, a rate control method of controlling the pulse rate is used in the medical treatment. In this case, whether or not the rate control is suitably performed is able to be determined by whether or not the numerical value of the pulse rate is within a suitable range. That is, the prescription medicine history information is useful for confirming the effect of the prescription medicine, and the change information of the pulse rate in chronological order is useful for confirming the effect of the rate control. Here, the change information of the pulse rate information in chronological order, as illustrated by D1 in FIG. 11A, may be a change graph in which a horizontal axis is a time and a vertical axis is the pulse rate. Furthermore, as with LF and HF, when the atrial fibrillation occurs, the value of the pulse rate is not able to be suitably obtained, and thus in FIG. 11A, the graph of the pulse rate is in a state of being discontinued in the rectangular frame. In addition, even when the rate control is performed, it is assumed that a plurality of inspections is performed, and thus it is useful to display the onset history information of the atrial fibrillation as illustrated in FIG. 11B.

In addition, according to the determination using the electrocardiogram, it is possible to determinately make a diagnosis with respect to the atrial fibrillation from the medical perspective. On the other hand, when the pulse wave information is used, as described later, although a method of reducing a noise is used, the accuracy may not be sufficient. Accordingly, the processing unit 230 may generate the browsing information including information which indicates the degree of reliability of the analysis result of the atrial fibrillation.

Here, the degree of reliability is a probability that the detected event is caused by the atrial fibrillation, and specifically, is an AF ratio described later, and is information obtained in the analysis processing on the basis of the pulse wave information. However, the degree of reliability is not limited thereto, and the other information may be used as the degree of reliability insofar as the information indicates the accuracy of the analysis processing of the atrial fibrillation based on the pulse wave information and the probability of the analysis result.

According to this, it is possible to suppress erroneous determination of the browsing user (the medical doctor or the like) who browses the browsing information. In the example of FIG. 7A, the AF ratio is displayed in a position indicated by A3 in a lower portion of the display screen. In the AF ratio, a horizontal axis is commonly used in time, and an onset degree of the atrial fibrillation (AF) at the corresponding time is displayed by a value of 0 percent to 100 percent.

Here, when the AF ratio is greater than or equal to 50, it is determined that the atrial fibrillation occurs. For this reason, in the simple presence or absence of the onset, there is no difference between the onset from 10 o'clock on February 8 and the onset after 4 o'clock in the afternoon on the same day. However, when the AF ratios are displayed in combination, there is a difference that the onset from 10 o'clock slightly exceeds 50, but the onset after 4 o'clock in the afternoon has a value of approximately 70. That is, the browsing user is able to perform determination by using preliminary information in which the onset after 4 o'clock in the afternoon has a certain degree of probability, but the onset from 10 o'clock may be erroneously determined by the biological information analyzing system 200. That is, by associating the degree of reliability with the analysis result of the atrial fibrillation, it is possible to increase the possibility of suitable determination of the browsing user.

3.2 Extraction of Monitoring Item Based on Setting Information

In the above description, information which is useful to be included in the browsing information, that is, the monitoring items are separately described. However, the monitoring item described above is not limited to a configuration in which all of the monitoring items are included in the browsing information at all times. For example, when the number of monitoring items excessively increases, it is difficult to view the screen, and thus the recognition of the information of the browsing user may be hindered. In addition, in a patient who has no onset history of the atrial fibrillation and just has a screening inspection, a result that there is no onset even when the patient had have an inspection before then or had not have an inspection is obtained, and thus the meaning of displaying the history information of the past is not important. Further, the medicine is not able to be prescribed, and thus the display of the prescription medicine history information is not necessary. That is, necessary items may be extracted from the monitoring items by using several methods, and the extraction result may be included in the browsing information.

Accordingly, the reception unit 210 may receive the setting information of the monitoring item relevant to the atrial fibrillation from the browsing user of the browsing information, the processing unit 230 may extract information corresponding to the monitoring item as the browsing information among the analysis results, and the output unit 250 may output the extracted browsing information.

The setting information of this case, for example, may be list information of the monitoring item which is desired to be browsed by the browsing user. According to this, it is possible to suitably present information desired by the browsing user, and thus it is possible for the browsing user to easily understand the analysis result.

However, as described above, it is assumed that there is a plurality of monitoring items, and thus it is considerably burdensome to select the item desired by the browsing user one by one. Accordingly, here, the setting information may be information indicating the state (the stage) of the patient.

As an example, the reception unit 210 may receive the setting information indicating that the user is in a screening inspection step relevant to the atrial fibrillation from the browsing user, and the processing unit 230 may extract at least one of the continuous onset time information of the atrial fibrillation, information indicating whether or not the onset of the atrial fibrillation ends in a predetermined time period, and the total onset time information of the atrial fibrillation as the monitoring item from the analysis result.

When the patient is in the screening inspection step, the importance of the onset history information of the atrial fibrillation as illustrated in FIG. 7B is low, and the result of one screening inspection as a target may be displayed. In this case, as described above, the information indicating the continuous onset time or the total onset time may be included in the browsing information. A display example of the browsing information in the screening inspection step is FIG. 10 described above. In FIG. 10, the horizontal width of the rectangular frame is the continuous onset time, and the total value thereof is the total onset time. In an example of FIG. 10, the total onset time is not displayed (the total value is not calculated), and thus, as necessary, the browsing user obtains the total onset time.

In addition, the atrial fibrillation is classified as paroxysmal atrial fibrillation and persistent atrial fibrillation, and the onset of the former naturally stops within 7 days, but the onset of the latter does not naturally stop within 7 days. When such classification is performed, the predetermined time period, for example, may be set to 7 days, and information indicating whether or not the onset ended within the time period may be presented. The information may be information such as "ended within 7 days" and "did not end within 7 days". However, as illustrated in FIG. 10 or the like, in a mode of definitely displaying the onset time period, whether or not the onset ends is able to be easily determined by the browsing user. For this reason, even when the information indicating whether or not the onset ends is not definitely displayed, it is sufficient to display the onset timing of the atrial fibrillation in the inspection time period (information in which the continuous onset time information is associated with the date and time).

In addition, as illustrated in FIG. 10, the display of information which is associated with the other information, for example, the body motion information, the autonomic nerve activity information, the event information, and the degree of reliability is not hindered.

In addition, the reception unit 210 may receive the setting information indicating that the user is in a medication effect confirmation step relevant to the atrial fibrillation from the browsing user, and the processing unit may extract at least one of the onset history information of the atrial fibrillation, the total onset time information of the atrial fibrillation (in a restricted sense, the total onset time information on an inspection date), the continuous onset time information of the atrial fibrillation, the prescription medicine history information indicating the medicine prescribed to the user, and the information indicating a change in the pulse rate information of the user in chronological order which is obtained on the basis of the pulse wave information as the monitoring item from the analysis result.

Display examples of the browsing information of this case are shown in FIG. 7A, FIG. 7B, FIG. 8A, FIG. 8B, FIG. 11A, and FIG. 11B. FIGS. 7A and 7B, and FIGS. 8A and 8B are a difference in the result of whether the patient has the sympathetic nerve dependent type atrial fibrillation or the vagus nerve dependent type atrial fibrillation, and have the same display items. In a medication step, the patient has a plurality of inspections, and thus the onset history information as illustrated in FIG. 7B is useful, and even in this step, the continuous onset time information and the total onset time information are important from a viewpoint of easiness of making a blood clot. In FIG. 7A, the continuous onset time information is displayed, and in FIG. 7B, the total onset time information is displayed as a line graph.

In addition, as illustrated by B2 in FIG. 7B, in order to confirm the medication effect, it is preferable to display the prescription medicine history information. In addition, when the rate control is performed, as described above, it may be desired to confirm whether or not the rate control is well performed, and thus as illustrated by D1 in FIG. 11A, the information indicating the change in the pulse rate in chronological order is useful.

In addition, the reception unit 210 may receive the setting information indicating that the user is in a catheter ablation effect confirmation step relevant to the atrial fibrillation from the browsing user, and the processing unit 230 may extract at least one of the onset history information of the atrial fibrillation, the total onset time information of the atrial fibrillation, and the continuous onset time information of the atrial fibrillation as the monitoring item from the analysis result.

The catheter ablation is a medical treatment method of cauterizing a part (for example, a portion causing a fast pulse) of the heart by inserting a catheter to the heart and by allowing electricity to flow through the catheter.

Figure 12A:
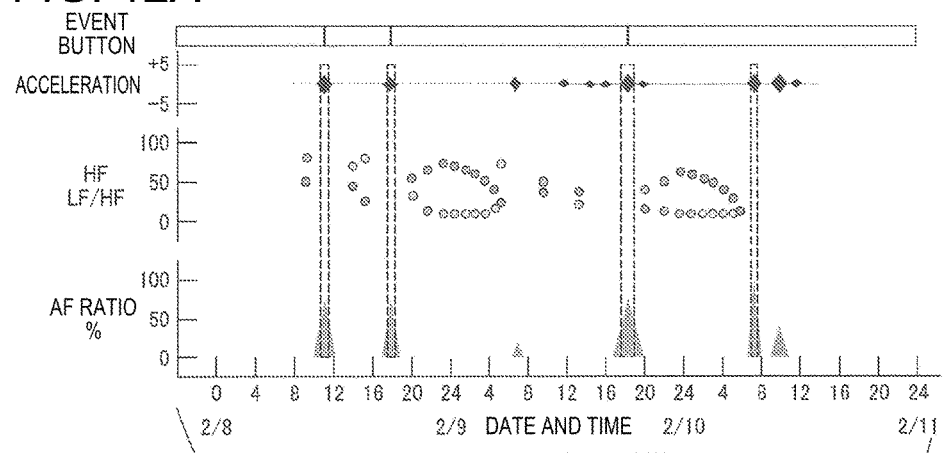
FIGS. 12A and 12B are screen examples at the time of presenting the browsing information.
Figure 12B:
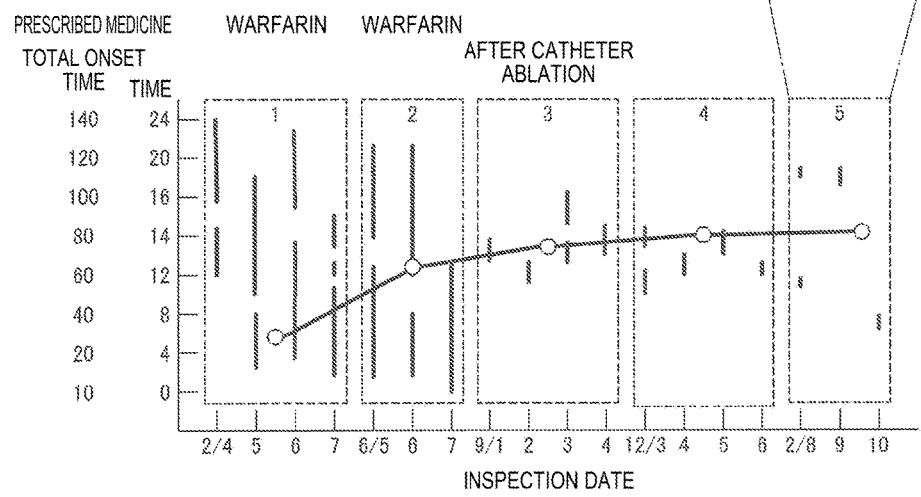

A display example of the browsing information of this case is FIGS. 12A and 12B. It is considered that the browsing user has a request for confirming the effect according to whether or not the symptomatic state is changed before and after the catheter ablation. For this reason, the onset history information illustrated in FIG. 12B may be displayed. In an example of FIG. 12B, it is found that the catheter ablation is performed between the second inspection and the third inspection, and thus the disease condition is improved. Furthermore, in the meaning of confirming the effect, as illustrated in FIG. 12B, information indicating a timing at which the catheter ablation is performed may be associated with the onset history information.

In addition, also in this case, the continuous onset time information and the total onset time information are important from a viewpoint of easiness of making a blood clot, in FIG. 12A, the continuous onset time information is displayed, and in FIG. 12B, the total onset time information is displayed as a line graph.

As described above, the setting information of the monitoring item may be information indicating a step of the medical treatment (or the inspection) of the patient. In this case, information which is useful to be presented in each step is able to automatically be selected on the system side even when the browsing user does not set the monitoring item one by one, and the burden on the browsing user is able to be reduced.

4. Determination Method of Atrial Fibrillation Based on Pulse Wave Information Finally, a method of determining (analyzing) the atrial fibrillation on the basis of the pulse wave information will be described. When the pulse wave is measured, a test subject may be freely moved during the measurement, and thus the influence of the body motion noise is easily included in the pulse wave signal. Even when the electrocardiogram is measured, there is a difference in degree between a case where the electrocardiogram is measured and a case where the pulse wave is measured, but the influence of the body motion noise may be included in the waveform signal of the electrocardiogram. Thus, it is extremely difficult to accurately measure the RR interval per beat due to the influence of the body motion noise. In this embodiment, a method is used in which the influence of the body motion noise is suppressed, and thus the atrial fibrillation is accurately detected even when the pulse wave information is used.

Figure 13:
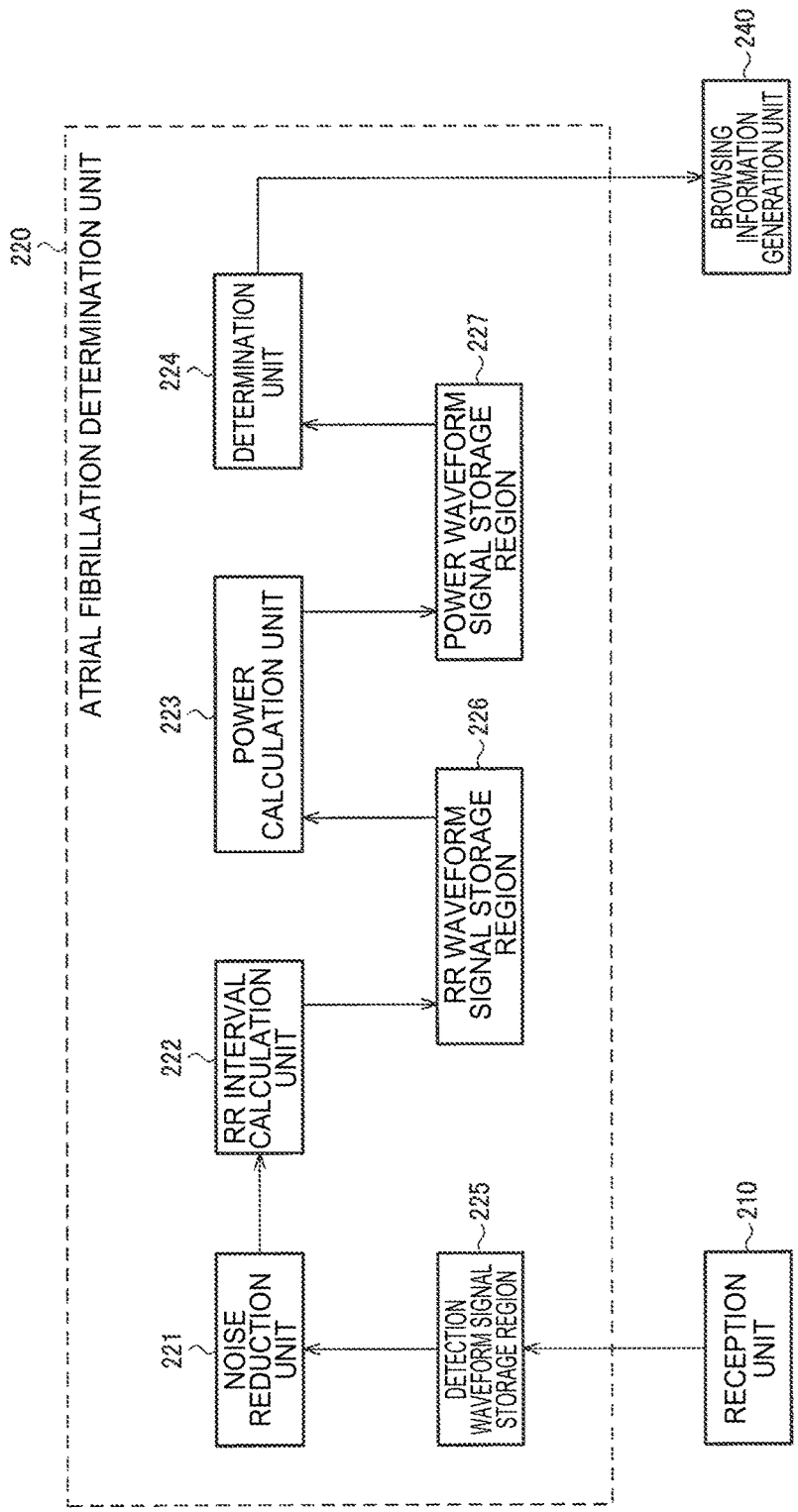
FIG. 13 is a specific configuration example of an atrial fibrillation determination unit.

The atrial fibrillation determination unit 220 of the processing unit 230, as illustrated in FIG. 13, includes a noise reduction unit 221, an RR interval calculation unit 222, a power calculation unit 223, and a determination unit 224, and is realized by each function configuration of a detection waveform signal storage region 225, an RR waveform signal storage region 226, and a power waveform signal storage region 227 which are a storage region for various data items.

The noise reduction unit 221 performs filter processing for reducing a body motion noise component other than a frequency band corresponding to the RR interval from a detection waveform signal L stored in the detection waveform signal storage region 225, and outputs the detection waveform signal L. The detection waveform signal storage region 225 and the noise reduction unit 221 function as an acquisition unit acquiring the detection waveform signal L used in the frequency analysis of the RR interval calculation unit 222.

Furthermore, in this processing, the body motion noise component is reduced, and the influence thereof is reduced from the detection waveform signal L, but it is not possible to accurately measure the RR interval to the extent of performing determination of the atrial fibrillation having the same degree as that of a case of using the electrocardiogram.

The RR interval calculation unit 222 cuts out a frame for each sampling with respect to the detection waveform signal L from which the body motion noise component is reduced by the noise reduction unit 221, and calculates a frequency spectrum by using frequency analysis (Short-Time Fourier transform (STFT) analysis) for a short period of time. Then, the RR interval calculation unit 222 calculates parameters corresponding to the RR interval for each frame on the basis of the calculated frequency spectrum, and stores an RR waveform signal FRR indicating a time change in the parameters in the RR waveform signal storage region 226.

In this example, the calculated parameters are a value indicating the average of the RR intervals within the frame (an average pulse wave RR interval), and for example, are a frequency which becomes the maximum peak of the frequency spectrum. Therefore, the RR waveform signal FRR indicates a time change in the average pulse wave RR interval. According to the processing of the RR interval calculation unit 222, it is possible to considerably reduce the influence of the body motion noise included in the RR waveform signal FRR even when the body motion noise is not completely removed by the noise reduction unit 221.

Figure 14A:
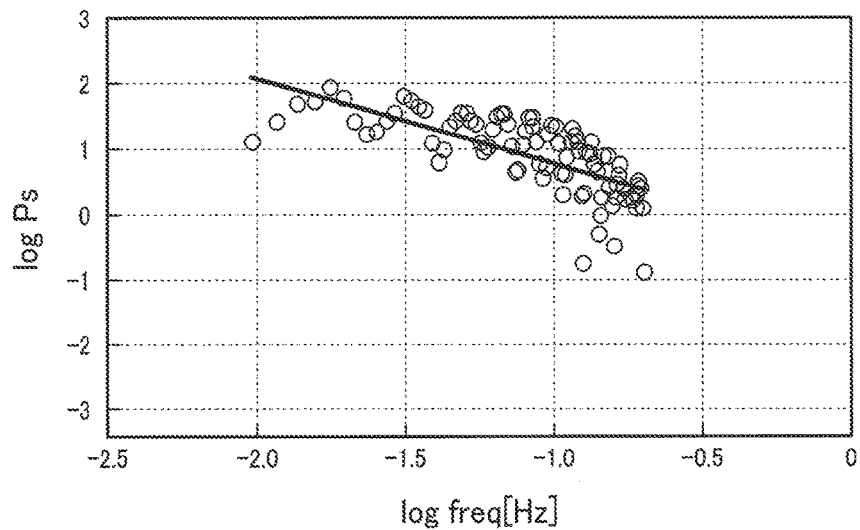
FIGS. 14A and 14B are graphs indicating a frequency analysis processing result based on an electrocardiographic RR interval.
Figure 14B:
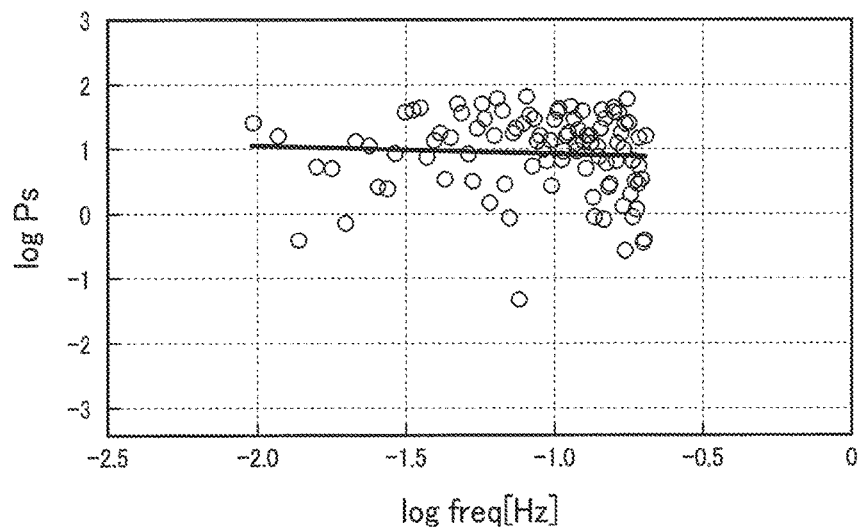
Figure 15A:
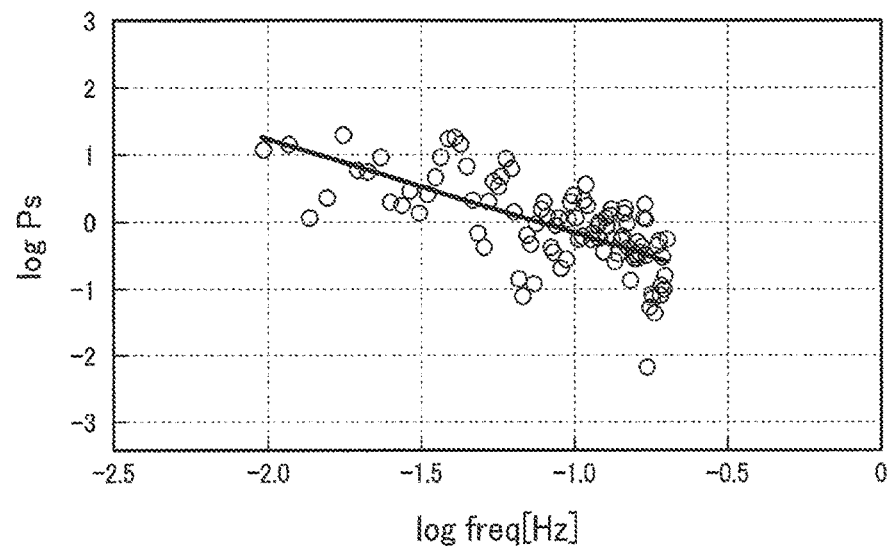
FIGS. 15A and 15B are graphs indicating a frequency analysis processing result based on an average pulse wave RR interval.
Figure 15B:
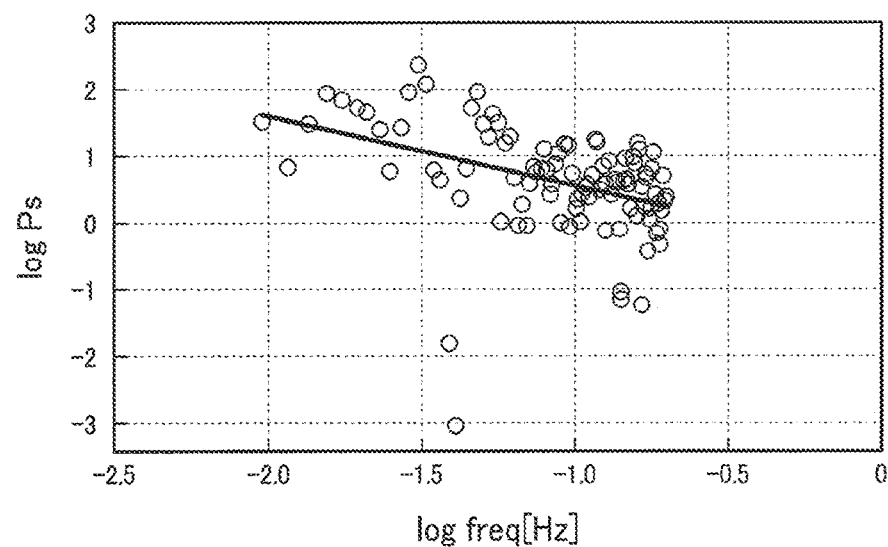

FIGS. 14A and 14B are graphs in which the frequency analysis is performed with respect to a waveform signal indicating a variation in an electrocardiographic RR interval at a band frequency of 0.01 Hz to 0.2 Hz in one frame to which the time period of 480 seconds is set, and a peak frequency and power are shown by being subjected to logarithmic conversion, and FIGS. 15A and 15B are graphs in which the same frequency analysis is performed with respect to the output of the RR interval calculation unit 222, that is, the average pulse wave RR interval. FIGS. 14A and 15A are graphs illustrating a case where the atrial fibrillation does not occur, and FIGS. 14B and 15B are graphs illustrating a case where the atrial fibrillation occurs.

As illustrated in FIGS. 14A and 14B, when the electrocardiographic RR interval is used, an intercept and a slope of a regression line are changed according to the presence or absence of the onset of the atrial fibrillation, and thus it is possible to determine the atrial fibrillation from the intercept and the slope. However, as illustrated in FIGS. 15A and 15B, when the average pulse wave RR interval is used, the body motion noise is able to be reduced, but a difference in the intercept and the slope according to the presence or absence of the onset is small, and thus it is difficult to perform the same determination.

However, when focused on a high frequency band of FIGS. 15A and 15B, a significant difference is generated due to a several fold increase in the power at the time when the atrial fibrillation occurs, compared to a case where the atrial fibrillation does not occur. Therefore, a change in the power of the frequency band may be an index for determining the presence or absence of the atrial fibrillation. In this embodiment, the atrial fibrillation is determined according to the change in the power.

The power calculation unit 223 performs the frequency analysis (the SIFT analysis) for a short period of time with respect to the RR waveform signal FRR stored in the RR waveform signal storage region 226, and calculates the power (hereinafter, referred to as band frequency power) of a part of the frequency band (hereinafter, referred to as a calculation frequency band) on the basis of the obtained frequency spectrum. The power calculation unit 223 stores a power waveform signal Pa indicating a time change in the calculated band frequency power in the power waveform signal storage region 227.

The determination unit 224 determines whether or not the power waveform signal Pa stored in the power waveform signal storage region 227 satisfies specific determination conditions, and outputs information corresponding to the determination result. In this example, the specific determination conditions indicate that a time at which the value of the power waveform signal Pa (the band frequency power) exceeds a threshold value Pth (for example, "1") determined in advance is greater than or equal to 50% of an observation time of 30 minutes from a determination time point in the past. That is, when the specific determination conditions are satisfied, it is determined that the atrial fibrillation occurs at the determination time point.

Furthermore, the specific determination conditions are able to be set in various manners, and when the value of the power waveform signal Pa exceeds the threshold value Pth for a certain period of time, it may be determined that the atrial fibrillation occurs. In addition, when the time at which the value of the power waveform signal Pa exceeds the threshold value Pth is less than 50% of the observation time of 30 minutes, it may be determined that the atrial fibrillation occurs in a condition where the number of times exceeding the threshold value Pth exceeds a certain number of times, or when an integral value of the band frequency power for 30 minutes exceeds a certain value, it may be determined that the atrial fibrillation occurs.

In addition, when the determination is not performed in real time, not the observation time of 30 minutes in the past, but, for example, an observation time of each 15 minutes before and after the determination time point may be used.

In this embodiment, among the observation times, the time at which the power exceeds Pth is able to be used as the AF ratio (the degree of reliability). That is, the determination unit 224 outputs the determination result of the atrial fibrillation to the browsing information generation unit 240, and may output the information of the AF ratio in combination.

Figure 16:
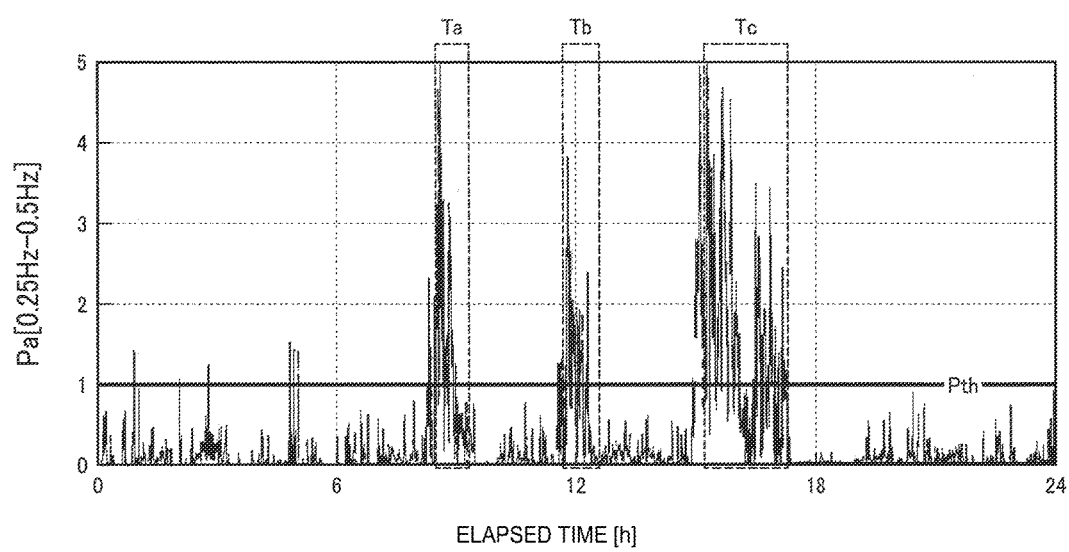
FIG. 16 is a diagram illustrating a time period determined as the atrial fibrillation.

FIG. 16 is a diagram illustrating a time period in which it is determined that the atrial fibrillation occurs. The waveform illustrated in FIG. 16, is an example of the waveform of the power waveform signal Pa as a predetermined frequency, and is a waveform obtained by detecting the pulse wave for 24 hours. Time periods Ta, Tb, and Tc indicate a time period in which the atrial fibrillation is determined by the time determination unit 224. In the time periods Ta, Tb, and Tc, as illustrated in FIG. 16, the value of the power waveform signal Pa increases.

Figure 17:
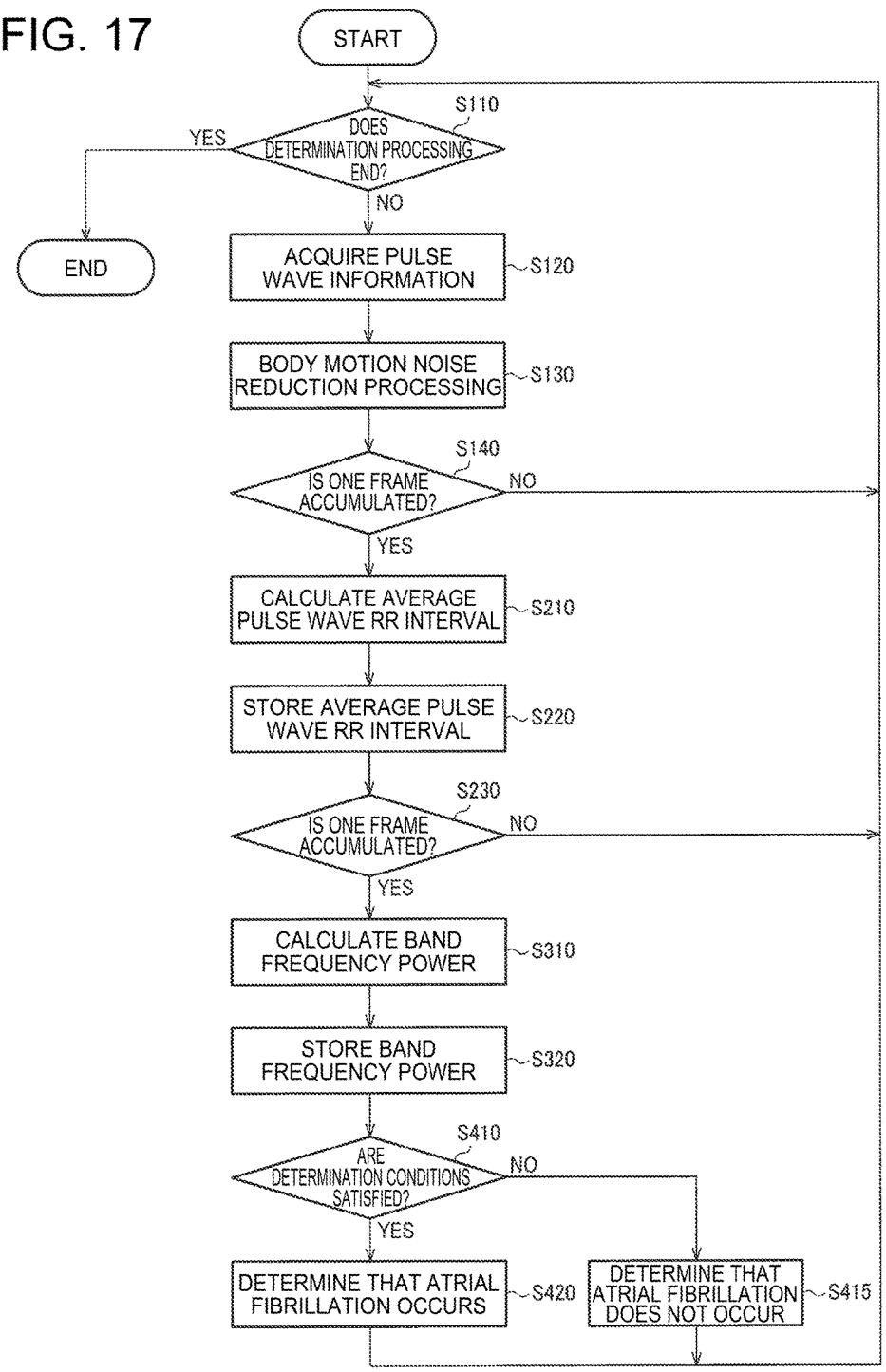
FIG. 17 is a flowchart illustrating atrial fibrillation determination processing (analysis processing).

FIG. 17 is a flowchart illustrating atrial fibrillation determination processing of this embodiment. First, when an instruction to start the determination processing of the atrial fibrillation is input by the user, the processing unit 230 starts the flow illustrated in FIG. 17. The processing unit 230 determines whether or not an instruction to end the determination processing is input by the user (Step S110). When the instruction to end the determination processing is input (Step S110; Yes), the processing unit 230 ends the determination processing of the atrial fibrillation.

When the instruction to end the determination processing is not input (Step S110; No), the processing unit 230 acquires the pulse wave information (the detection waveform signal L) from the reception unit 210 (Step S120), and performs body motion noise reduction processing by the noise reduction unit 221 (Step S130). At this time, the processing unit 230 stores the detection waveform signal L in the detection waveform signal storage region 225, and may store the detection waveform signal L which has been subjected to the body motion noise reduction processing.

The processing unit 230 determines whether or not one frame of the waveform signal which has been subjected to the body motion noise reduction processing is accumulated in a RAM (Step S140). When the one frame is not accumulated (Step S140; No), the processing unit 230 returns to Step S110 and continues the processing. In contrast, when the one frame is accumulated (Step S140; Yes), the processing unit 230 calculates the average pulse wave RR interval by the RR interval calculation unit 222 (Step S210).

The processing unit 230 stores the average pulse wave RR interval calculated by the RR interval calculation unit 222 in the RR waveform signal storage region 226 (Step S220). A time change in the average pulse wave RR interval stored in this storage region is the RR waveform signal FRR.

The processing unit 230 determines whether or not one frame of the RR waveform signal FRR stored in the RR waveform signal storage region 226 is accumulated (Step S230). When the one frame is not accumulated (Step S230; No), the processing unit 230 returns to Step S110 and continues the processing. In contrast, when the one frame is accumulated (Step S230; Yes), the processing unit 230 calculates the band frequency power by the power calculation unit 223 (Step S310).

The processing unit 230 stores the band frequency power calculated by the power calculation unit 223 in the power waveform signal storage region 227 (Step S320). A time change in the band frequency power stored in this storage region is the power waveform signal Pa.

The processing unit 230 determines whether or not the determination conditions of the atrial fibrillation which indicate that a value of greater than or equal to 50% of the band frequency power in 30 minutes of the past exceeds the threshold value Pth are satisfied by the determination unit 224 with reference to the stored power waveform signal Pa (Step S410). When it is determined that the determination conditions are not satisfied (Step S410; No), the processing unit 230 determines that the atrial fibrillation does not occur (Step S415), and returns to Step 110 and continues the processing.

In contrast, when it is determined that the determination conditions are satisfied (Step S410; Yes), the processing unit 230 determines that the atrial fibrillation occurs (Step S420), and returns to Step S110 and continues the processing.

Thus, in the atrial fibrillation determination unit 220 of this embodiment, it is possible to perform the determination of the atrial fibrillation while reducing the influence of the body motion noise by measuring the average pulse wave RR interval instead of the pulse wave RR interval per beat.

Furthermore, as described above, this embodiment is described in detail, and a person skilled in the art will easily understand that various modifications are able to be performed without substantially deviating from the new matter and the effect of the invention. Accordingly, all of these modification examples are included in the range of the invention. For example, in the specification or the drawings, a term which is described at least once along with a different term having a broader sense or the same sense is able to be substituted with the different term in any portion of the specification or the drawings. In addition, the configuration and the operation of the biological information analyzing system and the biological information processing system are not limited to those described in this embodiment, and are able to be variously modified.

What is claimed is:
1. A biological information analyzing system comprising:
  a reception unit receiving pulse wave information which is collected by a pulse wave measurement device configured to be worn by a user;
  a processing unit performing analysis processing with respect to atrial fibrillation of the user on the basis of the pulse wave information and generating browsing information of an analysis result of the analysis processing, the browsing information generated by the processing unit comprising information regarding a plurality of inspection results and total onset time information of the atrial fibrillation, the browsing information provided in a graphical user interface configured to be displayed on a display screen of a display device, the graphical user interface
    concurrently displaying the plurality of inspection results arranged chronologically along a date axis and a line graph that spans the plurality of inspection results and that indicates a change in the total onset time information of the atrial fibrillation,
    displaying each inspection result included in the plurality of inspection results as representing a block of time during which the pulse wave information is continuously captured by the pulse wave measurement device, and displaying adjacent inspection results included in the plurality of inspection results as being separated by an amount of time during which the pulse wave information is not captured by the pulse wave measurement device; and an output unit outputting the generated browsing information.

2. The biological information analyzing system according to claim 1, wherein the browsing information generated by the processing unit further includes continuous onset time information of the atrial fibrillation.

3. The biological information analyzing system according to claim 2, wherein the browsing information generated by the processing unit further includes information in which the continuous onset time information is associated with date and time.

4. The biological information analyzing system according to claim 1, wherein the reception unit receives body motion information of the user which is collected by the pulse wave measurement device or movement information of the user which is determined based on the body motion information, and the browsing information generated by the processing unit further includes information in which the body motion information or the movement information is associated with the analysis result of the atrial fibrillation.

5. The biological information analyzing system according to claim 1, wherein the browsing information further includes information in which autonomic nerve activity information obtained on the basis of the pulse wave information is associated with the analysis result of the atrial fibrillation.

6. The biological information analyzing system according to claim 1, wherein the browsing information generated by the processing unit further includes information which indicates a degree of reliability of the analysis result of the atrial fibrillation.

7. The biological information analyzing system according to claim 1, wherein the browsing information generated by the processing unit further includes information in which prescription medicine history information indicating medicine prescribed to the user is associated with the analysis result of the atrial fibrillation.

8. The biological information analyzing system according to claim 1, wherein the browsing information generated by the processing unit further includes information in which information indicating a change in pulse rate information of the user obtained on the basis of the pulse wave information in chronological order is associated with the analysis result of the atrial fibrillation.

9. The biological information analyzing system according to claim 1, wherein the browsing information generated by the processing unit further includes information in which event information indicating that the pulse wave measurement device has been operated is associated with the analysis result of the atrial fibrillation.

10. The biological information analyzing system according to claim 1, wherein the reception unit receives setting information of a monitoring item relevant to the atrial fibrillation from a browsing user of the browsing information, the processing unit extracts information corresponding to the monitoring item as the browsing information from the analysis result, and the output unit outputs the extracted browsing information.

11. The biological information analyzing system according to claim 10, wherein the reception unit receives the setting information indicating that the user is in a screening inspection step relevant to the atrial fibrillation from the browsing user, and the processing unit extracts at least one of continuous onset time information of the atrial fibrillation, information indicating whether or not the onset of the atrial fibrillation ends in a predetermined time period, and the total onset time information of the atrial fibrillation as the monitoring item from the analysis result.

12. The biological information analyzing system according to claim 10, wherein the reception unit receives the setting information indicating that the user is in a medication effect confirmation step relevant to the atrial fibrillation from the browsing user, and the processing unit extracts at least one of onset history information of the atrial fibrillation, the total onset time information of the atrial fibrillation, continuous onset time information of the atrial fibrillation, prescription medicine history information indicating medicine prescribed to the user, and information indicating a change in pulse rate information of the user obtained on the basis of the pulse wave information in chronological order as the monitoring item from the analysis result.

13. The biological information analyzing system according to claim 10, wherein the reception unit receives the setting information indicating that the user is in a catheter ablation effect confirmation step relevant to the atrial fibrillation from the browsing user, and the processing unit extracts at least one of onset history information of the atrial fibrillation, the total onset time information of the atrial fibrillation, and continuous onset time information of the atrial fibrillation as the monitoring item from the analysis result.

14. A biological information processing system, comprising:

a pulse wave measurement device which is configured to be worn by a user and collects pulse wave information; and an information processing device, wherein the information processing device, includes a reception unit receiving the pulse wave information collected by the pulse wave measurement device, a processing unit performing analysis processing with respect to atrial fibrillation of the user on the basis of the pulse wave information and generating browsing information of an analysis result of the analysis processing, the browsing information generated by the processing unit comprising information regarding a plurality of inspection results and total onset time information of the atrial fibrillation, the browsing information provided in a graphical user interface configured to be displayed on a display screen of a display device, the graphical user interface concurrently displaying the plurality of inspection results arranged chronologically along a date axis and a line graph that spans the plurality of inspection results and that indicates a change in the total onset time information of the atrial fibrillation, displaying each inspection result included in the plurality of inspection results as representing a block of time during which the pulse wave information is continuously captured by the pulse wave measurement device, and displaying adjacent inspection results included in the plurality of inspection results as being separated by an amount of time during which the pulse wave information is not captured by the pulse wave measurement device, and an output unit outputting the generated browsing information.

15. The biological information analyzing system according to claim 1, wherein the graphical user interface further displays, for each inspection result included in the plurality of inspection results, information identifying a medicine prescribed to the user during a respective block of time associated with each inspection result.

16. The biological information processing system according to claim 14, further comprising:

a second information processing device operated by a browsing user, wherein the second information processing device performs a browsing request of the analysis result with respect to the information processing device, the output unit of the information processing device outputs the browsing information to the second information processing device according to the browsing request, and the second information processing device displays the graphical user interface including the browsing information output from the information processing device on the display screen of the display device.

* * * * *